United States Patent
Makower et al.

(10) Patent No.: US 9,492,310 B2
(45) Date of Patent: Nov. 15, 2016

(54) ADJUSTABLE TONGUE RETAINING ORAL APPLIANCE

(71) Applicant: SLEEPY, INC., Mountain View, CA (US)

(72) Inventors: Joshua Makower, Los Altos Hills, CA (US); Earl A. Bright, II, Los Altos, CA (US); Eric Goldfarb, Belmont, CA (US); William Facteau, Atherton, CA (US); Ravinder D. Pamnani, Belmont, CA (US); Joseph Catanese, III, San Leandro, CA (US); Theodore Bender, San Anselmo, CA (US); Imraan Aziz, Oakland, CA (US); Kyle Lamson, San Francisco, CA (US); Michael Strasser, San Francisco, CA (US); Jason Hegener, San Francisco, CA (US)

(73) Assignee: Sleepy, Inc., Mountain View, CA (US)

( * ) Notice: Subject to any disclaimer, the term of this patent is extended or adjusted under 35 U.S.C. 154(b) by 276 days.

(21) Appl. No.: 14/044,679

(22) Filed: Oct. 2, 2013

(65) Prior Publication Data

US 2014/0090654 A1      Apr. 3, 2014

Related U.S. Application Data

(60) Provisional application No. 61/708,914, filed on Oct. 2, 2012.

(51) Int. Cl.
*A61F 5/56* (2006.01)
*A63B 71/08* (2006.01)

(52) U.S. Cl.
CPC ............ *A61F 5/566* (2013.01); *A63B 71/085* (2013.01)

(58) Field of Classification Search
CPC ........... A61F 5/56; A61F 5/566; A61F 2/00; A61F 2/20; A61F 2005/563; A63B 71/085; A63B 2071/088; A63B 2208/12; A61C 7/08
See application file for complete search history.

(56) References Cited

U.S. PATENT DOCUMENTS 4,198,967 A * 4/1980 Dror ...................... A61B 17/30
                                                            128/207.14

* cited by examiner

*Primary Examiner* — Ophelia A Hawthorne

(57) ABSTRACT

A device for receipt in a user's mouth includes a tongue engagement element having a front region, a rear region, and side regions that define an opening for receiving a user's tongue, means for retaining the user's tongue in a forward position, and means for changing the size of the opening. The tongue engagement element is shaped such that when placed in a user's mouth, the rear region extends over the user's tongue and the front region extends under the user's tongue. A method of securing a tongue engagement element in a user's mouth includes moving an expanded tongue engagement element under a front region of a tongue and over a rear region of the tongue, and allowing the tongue engagement element to return toward a non-expanded state. The tongue engagement element acts to resist rearward motion of the tongue.

6 Claims, 37 Drawing Sheets

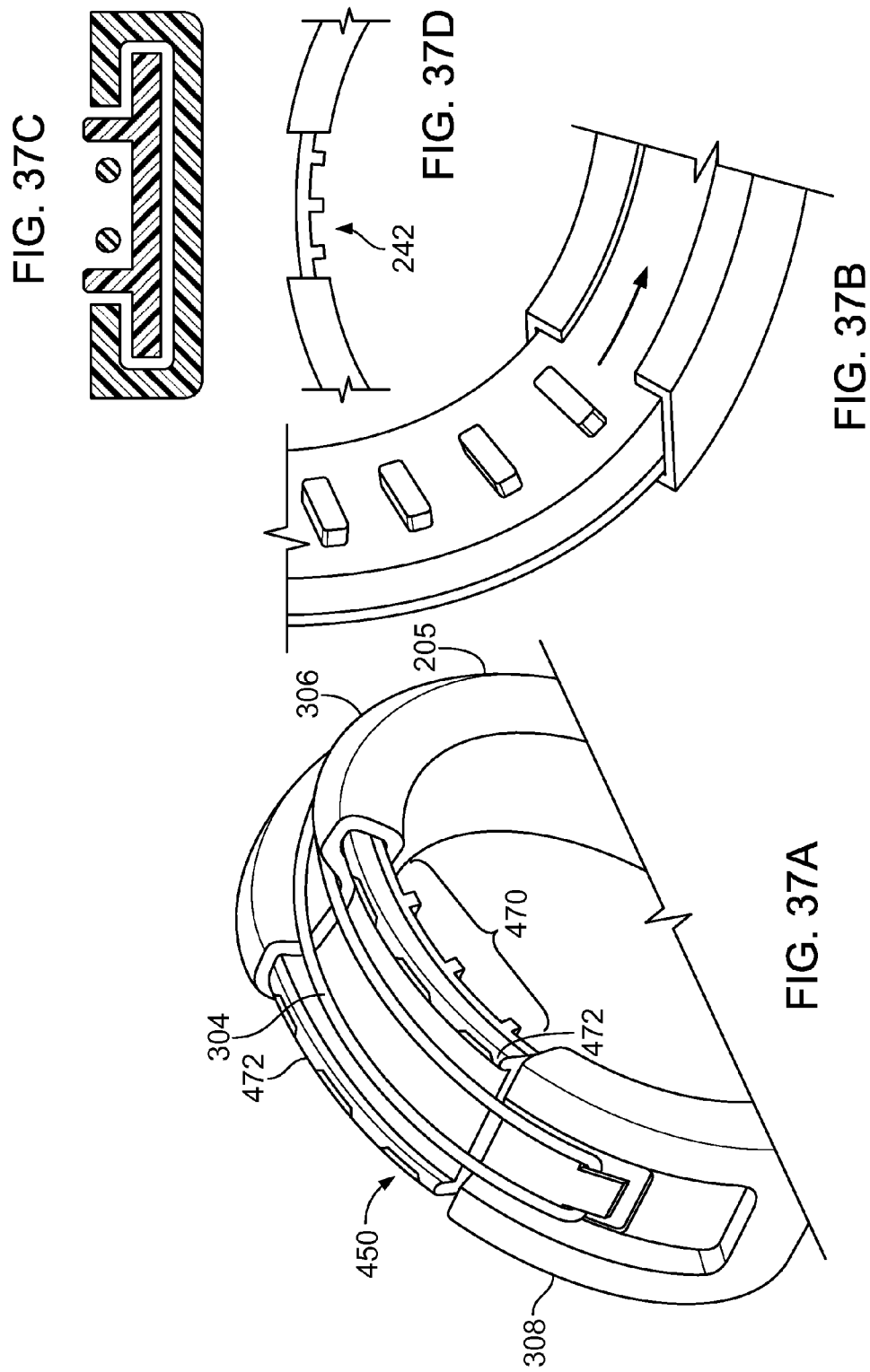

ADJUSTABLE TONGUE RETAINING ORAL APPLIANCE

CROSS-REFERENCE TO RELATED APPLICATION

This application claims priority from U.S. Provisional Application No. 61/708,914, filed Oct. 2, 2012, and titled "ADJUSTABLE TONGUE RETAINING ORAL APPLIANCE," hereby incorporated by reference in its entirety.

TECHNICAL FIELD

This description relates to an adjustable oral appliance for retaining the tongue forward to open the airway during exercise or sleep, and to PCT Publication No. WO 2011/156396, titled "TONGUE RETAINING ORAL APPLIANCE," hereby incorporated by reference in its entirety.

BACKGROUND

Snoring is vibration caused by a narrowed or constricted airway during sleep. Narrowing or constriction of the airway can happen for many reasons including large tonsils, nasal congestion, a long soft palate or uvula, excessive flabby tissue, and cartilage deformities in the nose or nasal structure. Snoring can also be accompanied by sleep apnea. People with sleep apnea are deprived of oxygen due to a complete blockage of the airways. Obstructive sleep apnea (OSA) is the most common type of sleep apnea and is caused by an obstruction, which stops the airflow in the nose and mouth. A common cause of snoring and OSA is the tongue muscle relaxing too much during sleep, blocking the airways.

OSA is characterized by repetitive complete or partial closure of the upper airway during sleep resulting in sleep fragmentation and oxygen desaturation. Numerous risk factors including male gender, obesity, ethnicity and craniofacial structure have been identified as increasing susceptibility to this disorder. OSA causes daytime sleepiness, impaired neurocognitive function, and impaired quality of life. It has been linked to cardiovascular and cerebrovascular disease, and increased risk for motor vehicle accidents.

Therapeutic options include lifestyle changes targeted at reversible risk factors (e.g. weight loss), continuous positive airway pressure (CPAP), oral devices, or surgery. CPAP pressurizes the upper airway and is applied via a nose or face mask worn during sleep. A mandibular advancement splint (MAS) is an oral device worn during sleep that protrudes the mandible. Another type of oral device is the tongue retaining device, which consists of a plastic bulb into which the tongue is placed and held out of the mouth during sleep by suction. Surgery aims to overcome or bypass regions of airway obstruction. Surgical approaches include nasal procedures, soft palate surgery, tongue base surgery, maxillofacial surgery, and tracheotomy.

SUMMARY

The oral appliance decreases the severity of OSA and snoring by maintaining the tongue in its forward position, away from engagement with the soft palate and airway. The oral appliance is a single patient, non-invasive device designed for the treatment of sleep apnea and snoring intended for home use. The oral appliance is designed to be self-administered by the user prior to sleep and worn throughout the night. The user inserts their tongue into the frame of the oral appliance and the tongue is engaged and maintained in its forward position by an atraumatic tongue retention system on the frame so that the tongue does not slip backwards. The frame can incorporate an expansion mechanism that assists installation and adjusts per user anatomy and tongue position. An optional installation tool is provided to expand the frame during installation. The housing is fastened forward in the mouth through the use of an anchor, which sits between two of the front incisors. A pull tab is provided to assist handling of the device. The anchor and pull tab are connected to the frame via an attachment member. Once placed, the patient may breathe normally through their mouth or nose without obstruction. Upon waking, the device is simply removed from the mouth.

According to one aspect, a device for receipt in a user's mouth includes a tongue engagement element having a front region, a rear region, and side regions that define an opening for receiving a user's tongue. The side regions extend back and outward from the front region to the rear region such that the rear region is wider than the front region. The tongue engagement element is adjustable to change the size of the opening. The front region has an upper surface and the rear region has a lower surface. The rear region extends upward relative to the front region such that the lower surface is spaced from the upper surface to receive the user's tongue therebetween. The element is shaped such that when placed in a user's mouth, the rear region extends over the user's tongue and the front region extends under the user's tongue.

Embodiments of this aspect may include one or more of the following features.

The rear region is split to permit expansion of the tongue engagement element. The tongue engagement element is biased toward a non-expanded state. The rear region includes a tongue retention system, for example, bristles. The rear region is configured to extend over the user's tongue to rest on the tongue. The rear region is generally arch shaped with piers that include a tongue retention system. The rear region is configured to curve over the user's tongue to engage the sides of the user's tongue with the tongue retention system. The tongue engagement element has a length, L, that is greater than a width, W1. The device includes a biasing member. A member connects the element and an anchor. The member is configured to be positioned between two teeth.

According to another aspect, a method of securing a tongue engagement element in a user's mouth includes moving an expanded tongue engagement element under a front region of a tongue and over a rear region of the tongue, and allowing the tongue engagement element to return toward a non-expanded state. The tongue engagement element acts to resist rearward motion of the tongue.

Embodiments of this aspect may include one or more of the following features.

A retention system of the tongue engagement element engages the tongue. The retention system acts to resist rearward motion of the tongue. The method includes placing a member connecting the tongue engagement element to an anchor between two teeth. The method includes positioning the anchor between the user's teeth and the user's lip. The distal tip of the tongue is at rest while the pharyngeal portion of the tongue remains tensioned.

According to another aspect, a device for receipt in a user's mouth includes a tongue engagement element having a front region, a rear region, and side regions that define an opening for receiving a user's tongue, means for retaining the user's tongue in a forward position, and means for changing the size of the opening. The tongue engagement element is shaped such that when placed in a user's mouth, the rear region extends over the user's tongue and the front region extends under the user's tongue. The oral appliance is an intra-oral design that reduces drooling and expulsion of the device during sleep. The atraumatic tongue retention system provides a passive means of engaging the tongue. The functional position of the oral appliance maintains normal anatomic positioning of the jaws relative to each other during lingual advancement. The anchor provides a simple, non-customized engagement mechanism with the lower jaw. The oral appliance allows the user to swallow while the appliance is in place. The oral appliance is a re-usable and disposable (also known as resposable) non-invasive design that reduces the need for anatomy altering surgery or implants.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 26A-26E, 27, 28A, 28B, 29, 30A-30C, 31-33, 34A, 34B, 35A, 35B, 36A, 36B, 37A-37D, 38, 39, 40A, 40B, 41, and 42 illustrate alternative embodiments of an expansion mechanism.

DETAILED DESCRIPTION

Figure 1:
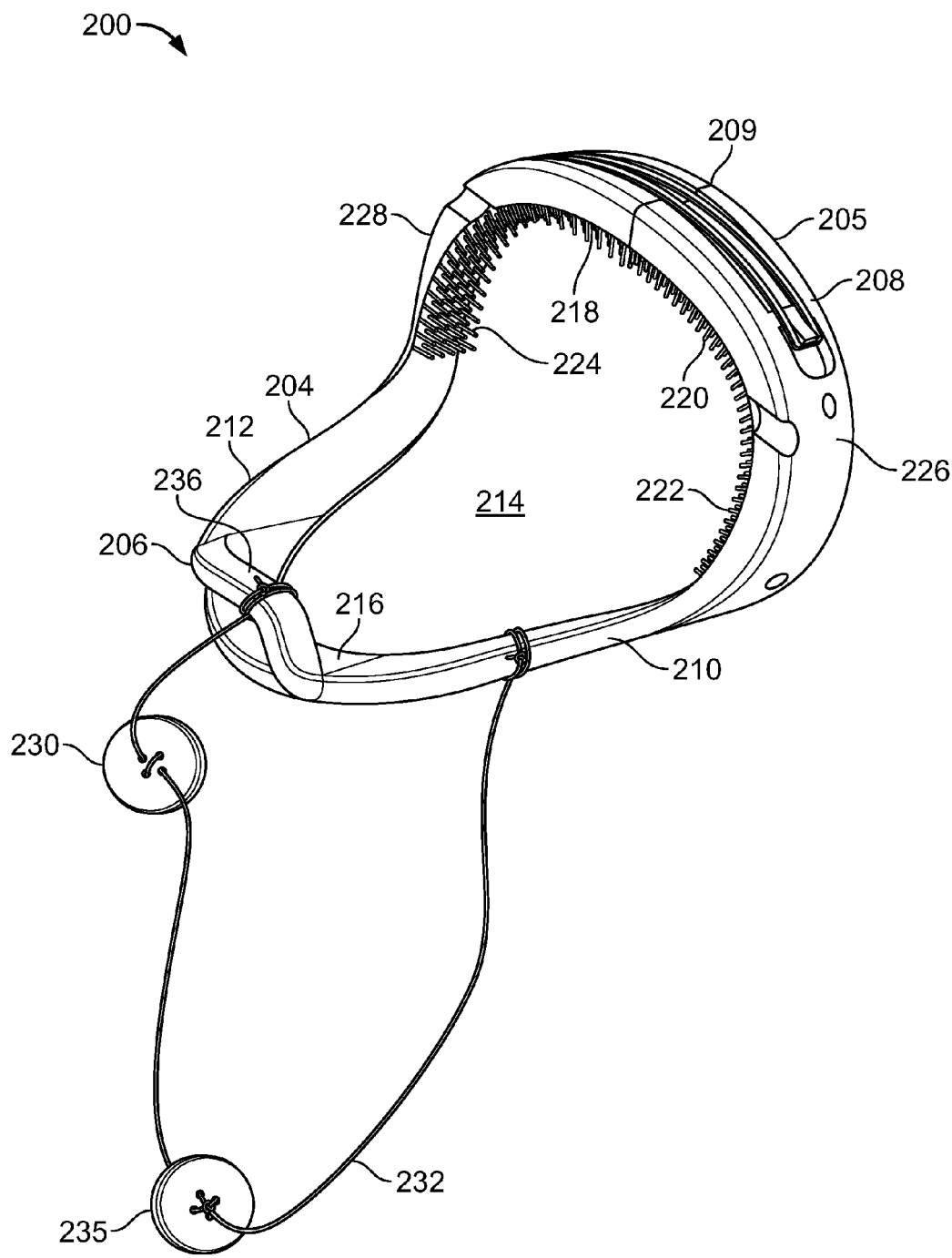
FIG. 1 is an isometric view of an oral appliance.
Figure 2B:
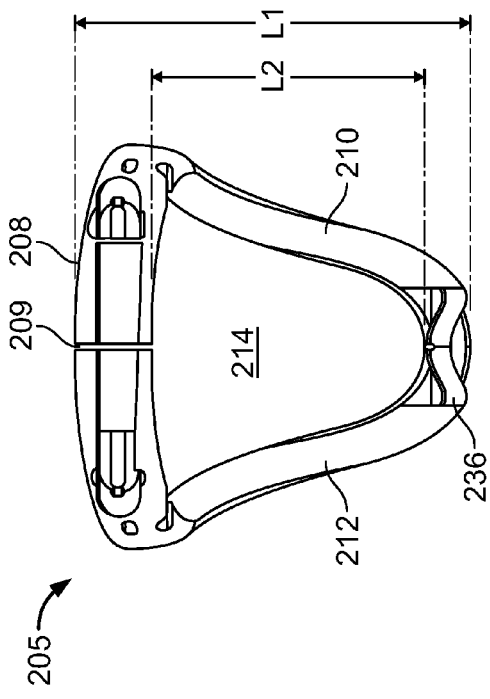
FIGS. 2A-2D are isometric, top, front, and side views of a frame of the oral appliance.
Figure 2A:
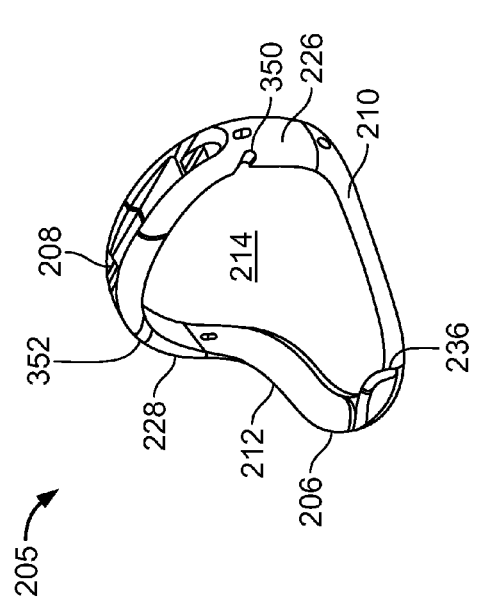
Figure 2D:
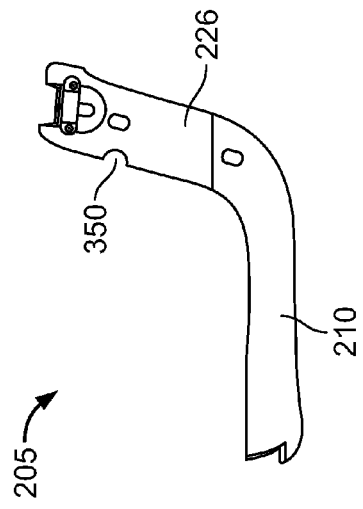
Figure 2C:
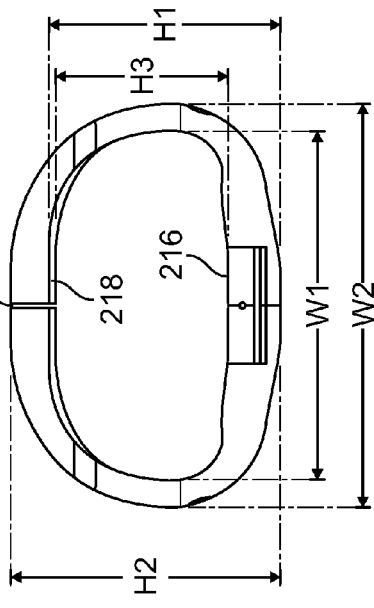

A tongue retaining oral appliance has a tongue retention system that limits movement of the tongue toward the user's throat to maintain an open air passageway when the user is exercising or sleeping, such as to minimize or eliminate snoring and/or treat obstructive sleep apnea. To promote user comfort, the tongue retention system has a small contact area, and contacts the tongue in a region of the tongue that limits the gag reflex, limits inducing salivation, and allows the tongue to move during swallowing to contact the upper palate. To further promote user comfort, in some embodiments, the tongue retention system contacts the top of the tongue lightly, that is does not depress the top of the tongue, when the user is falling asleep, and applies a retraining force to the tongue as the tongue begins to move toward the user's throat as the user falls asleep. For use during exercise, the tongue retention system can depress the tongue more if needed. The oral appliance can be sold over-the-counter as it does not require custom fitting by a professional.

The appliance can be provided, for example, in one or more standard sizes—small, medium and large. The user's size can be determined by the spacing between the second molars #18, 31, or a self-assessment of the users tongue size. The appliance can be expandable to provide more size differentiation and aid in placement of the appliance on the user's tongue.

Referring to FIGS. 1 and 2A-2D, an embodiment of an oral appliance 200 is in the form of a tongue engagement element 204 for receipt on a user's tongue. The tongue engagement element 204 has a frame 205 with a front region 206, a rear band region 208, and side regions 210, 212. The front, rear and side regions form a loop defining an opening 214 for receiving the user's tongue. The side regions 210, 212 extend back and outward from the front region 206 to the rear region 208 such that the rear region 208 is wider than the front region 206. The front region 206 has an upper surface 216 and the rear region 208 has a lower surface 218 with the rear region 208 extending upward relative to the front region 206 with respect to a user's mouth such that the lower surface 218 is spaced from the upper surface 216 to receive the user's tongue therebetween.

The rear region 208 includes a tongue retention system 220, for example, bristles, which extends inward from the lower surface 218 to engage the top of the user's tongue and from inner surfaces 222, 224 of the rear region 208 to engage the sides and part of the underside of the user's tongue. The bristles that engage the sides and part of the underside of the user's tongue help to secure the tongue against the bristles that engage the top of the user's tongue. The rear region 208 is generally arch shaped with piers 226, 228 such that the rear region 208 curves over the tongue. The piers 226, 228 include the inner surfaces 222, 224, respectively, that include the structures 220 for engaging the sides of the user's tongue. The rear region 208 is split at 209 to permit the size of opening 214 to be adjusted, as discussed further below.

Figure 3A:
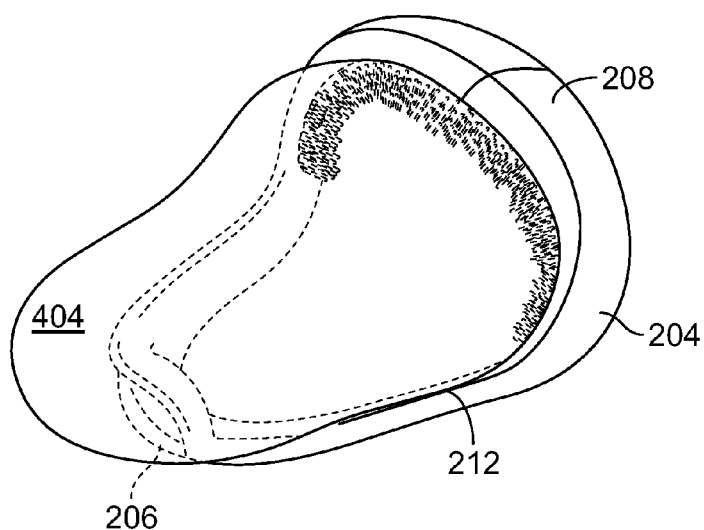
FIG. 3A-3C illustrates the frame on a tongue, within lower teeth, and on a tongue within lower teeth.
Figure 3B:
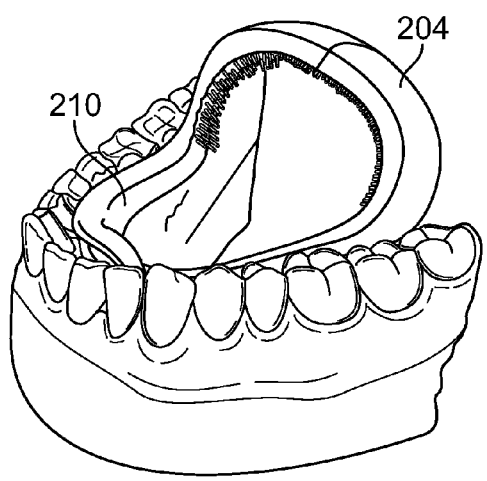
Figure 3C:
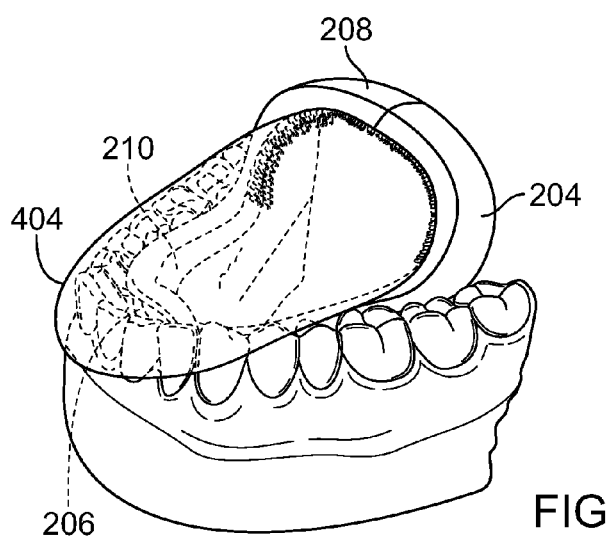

Referring to FIGS. 3A-3D, the tongue engagement element 204 is shaped such that when placed in a user's mouth the element 204 does not interfere with the user's normal bite, that is does not pull the user's lower jaw out of alignment. The element 204 wraps around the tongue 404 with the rear region 208 extending over the user's tongue to rest on the tongue, the side regions 210, 212 extending along the floor of the user's mouth cavity under the tongue, and the front region 206 extending under the user's tongue. In FIG. 3B, the tongue is removed from the figure to show the front region 206 and side regions 210, 212 sitting within the borders of the dentition.

Figure 4:
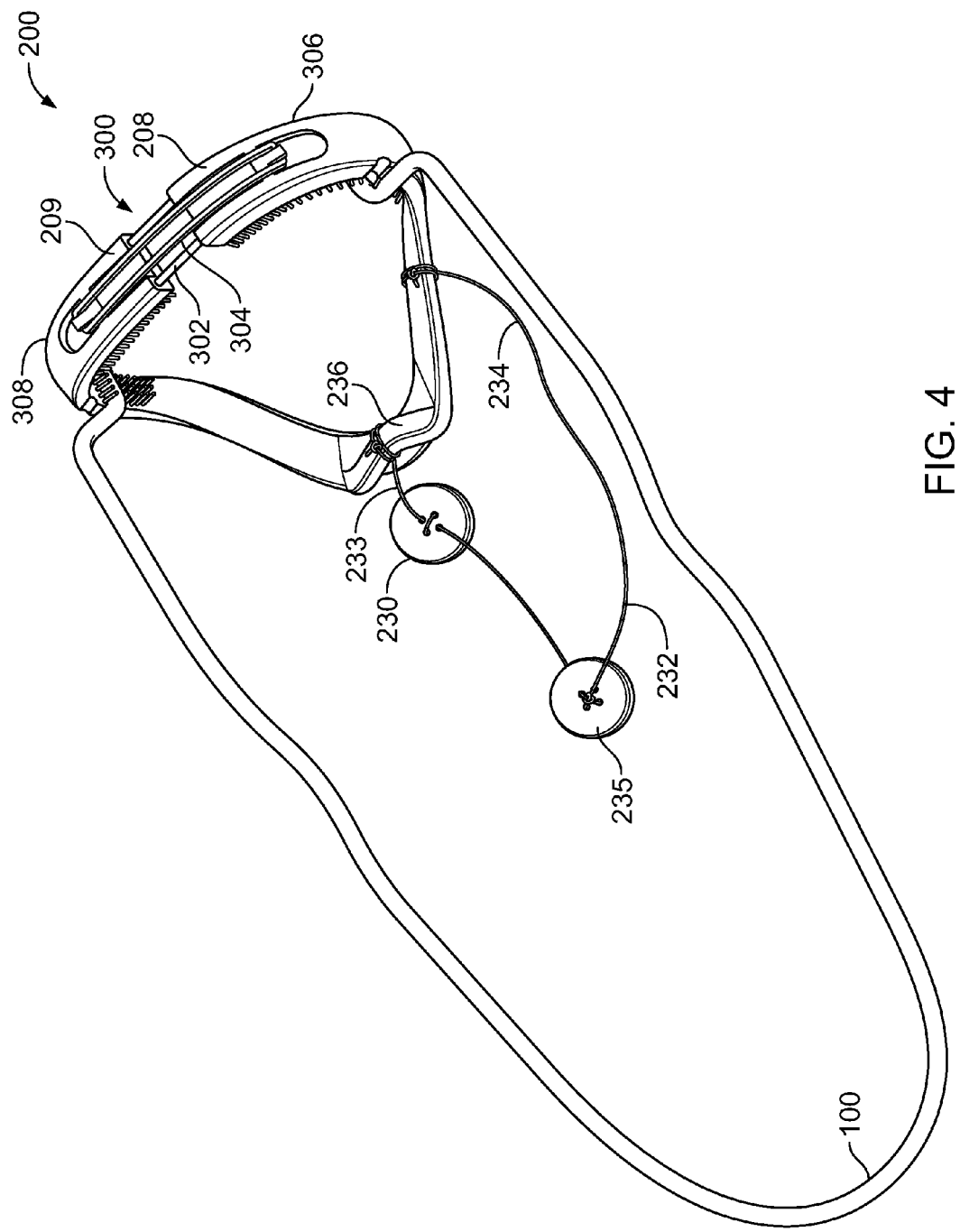
FIGS. 4 and 5 illustrate the oral appliance expanded by an installation tool.
Figure 5:
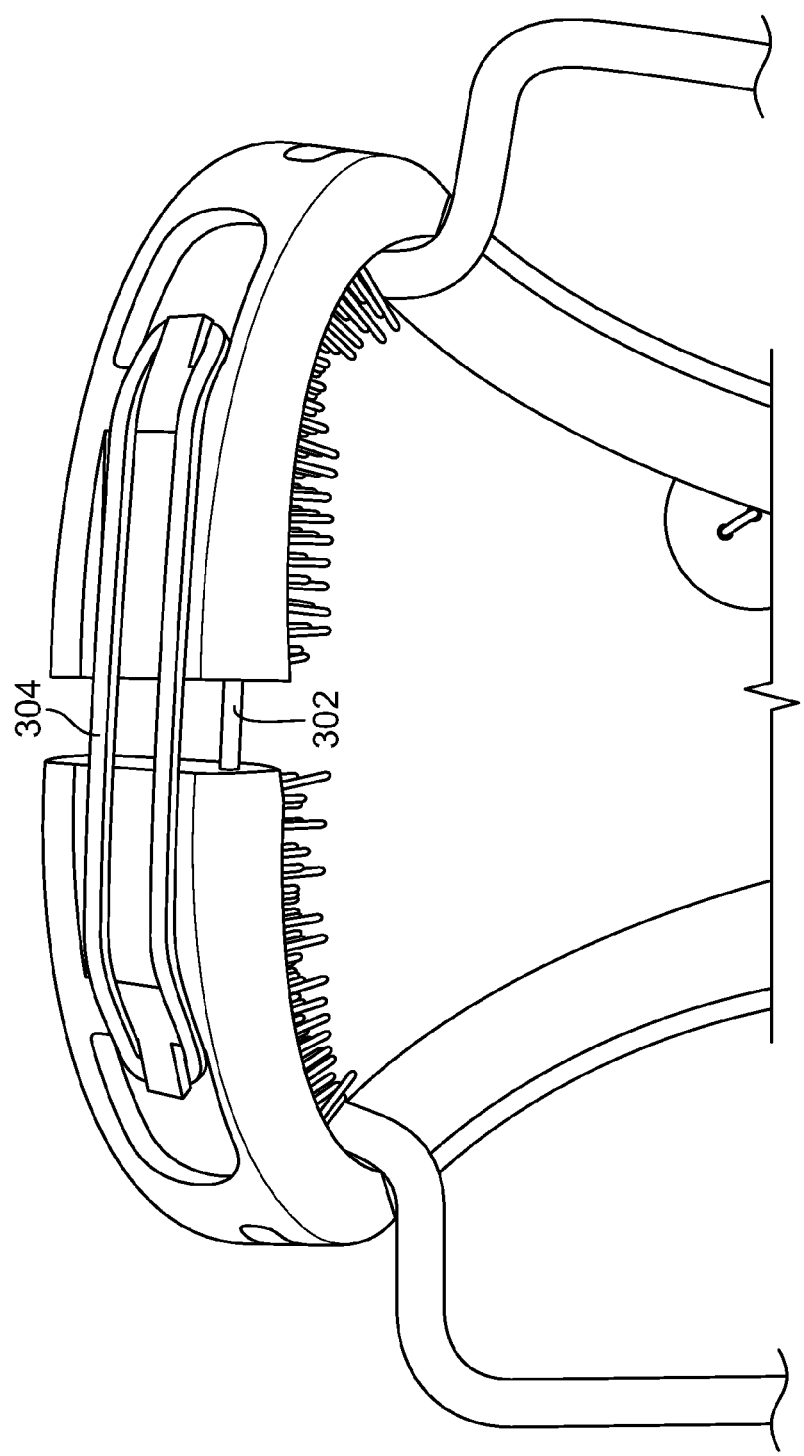
Figure 6:
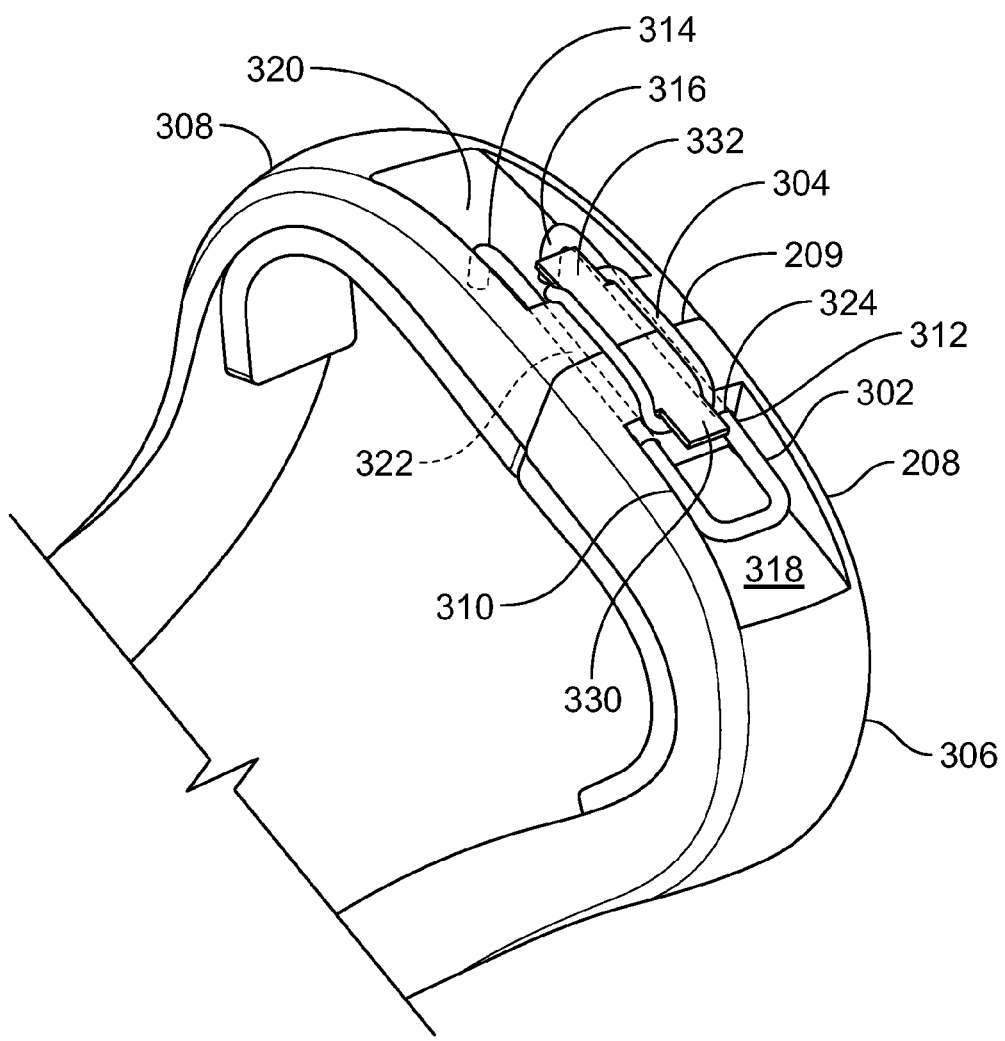
FIG. 6 illustrates one embodiment of an expansion mechanism of the oral appliance.

Referring to FIGS. 4-6, to make the tongue engagement element 204 expandable, the rear region 208 includes an expansion element 300 embedded therein and the front region 206 has some flexibility such that the u-shaped portion widens as the rear region expands. Alternatively or in combination, the piers 226, 228 and/or the junctions of pier 226 with side region 210 and pier 228 with side region 212, respectively, can have some flexibility to accommodate the rear region expansion. In the embodiment of FIGS. 4-6, the oral appliance is made from PEBAX and the expansion element 300 includes a u-shaped wire guide 302 and a biasing member 304, for example, a silicone O-ring or an orthodontic elastic or rubber band.

The frame 205 can be made from, for example, FDA silicone, stainless steel, dental acrylic, thermoplastic elastomer (TPE), Polyethylene terephthalate (PET), Low-density polyethylene (LDPE), PEBAX, TEXIN, and nylon. The split 209 divides the rear region 108 into two parts 306, 308, and the wire guide 302 and biasing member 304 traverse the split 209. The wire guide 302 has arms 310, 312 with bent ends 314, 316 or without bent ends. The rear region 208 defines grooves 318, 320 for receiving the wire guide 302, with arms 310, 312 extending through bores 322, 324. The wire guide 302 can be fixed to part 308, for example, at bent ends 314, 316, and slidable relative to part 306. Alternatively, the wire guide 302 can be slidable relative to both parts 306, 308. The biasing member 304 extends over the rear region 208 and hooks over rear region tabs 330, 332. The biasing member can be, for example, a silicone O-ring, a die cut band of silicone or urethane, small diameter stainless steel or nitinol coil, or a non-latex orthodontic band, and the wire guide can be formed, for example, of electro-polished stainless steel. In a preferred embodiment, the force level of compression from the expansion mechanism is about 0.5 to 1 N at the minimum expansion and about 1.5 N at the maximum expansion.

The wire guide 302 acts to linearly guide the parts 306, 308 during expansion and contraction of the rear region 208 and provides rigidity to the frame 205 during expansion and contraction of the frame. For this embodiment, the wire guide limits the expansion mechanism to a single degree of freedom, for example along the axis of expansion. By allowing expansion on this axis and limiting motion in other directions, greater gripping ability is maintained. The biasing member 304 maintains a compressive force on the frame 205 when the frame expands, acting to bias the rear region 208 toward the un-expanded, closed position such that upon removal of an expansion force, the rear region 208 returns toward its un-expanded, closed position. The ability to expand the tongue engagement element 204 provides greater size variability, improved contact with the tongue, as well as aiding insertion of the tongue engagement element 204 onto the tongue. As discussed further below, the user can employ an installation tool 100 to expand the tongue engagement element 204 to aid in placing the oral appliance 200 on their tongue.

To secure the oral appliance 200 in the user's mouth, this embodiment of the oral appliance 200 includes an anchor 230, a pull tab 235, and an attachment member 232, for example, dental floss, connecting the anchor 230 and pull tab 235 to the tongue engagement element 204. In use, a portion 233 of the attachment member 232 between the tongue engagement element 204 and the anchor 230 is positioned between the user's two front lower teeth, and a portion 234 of the attachment member 232 between the tongue engagement element 204 and the pull tab 235 is positioned over the user's lower front teeth. Portion 234 acts as a safety to prevent the anchor 230 and pull tab 235 from becoming detached from the oral appliance 200 if the portion 233 of the attachment member 232 becomes damaged. The pull tab 235 aids in placing the portion 233 between the front lower teeth, as discussed below. The attachment member 232 can be made, for example, from ultra-high molecular weight polyethylene (UHMWPE), Gore-Tex, EPTFE, high strength surgical suture, or small diameter stainless steel braided wire. The anchor 230 and pull tab 235 can be made, for example, from PEBAX, 72 Shore D. The selected durometer provides some flexibility and softness to the anchor and pull tab. The PEBAX material has good tear resistance, which is useful to reduce the risk of "cheese cutting" from tension on the attachment member 232. Other materials could be 60 to 80 Shore D PEBAX, TEXIN, or Urethane. A harder anchor and pull tab can be fabricated from ABS, polycarbonate, or stainless steel.

Figure 3D:
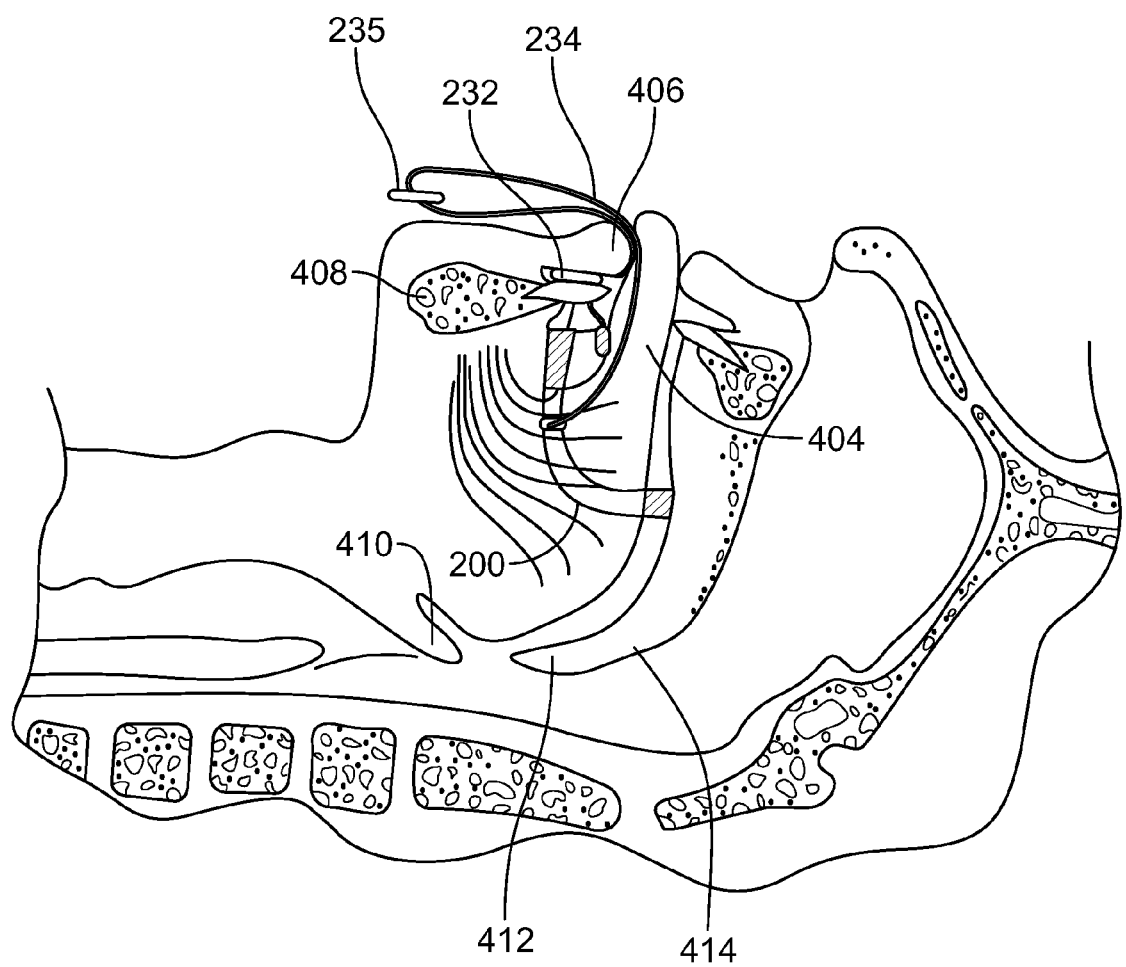
FIG. 3D is a side view of the oral appliance in a mouth while the user is supine.

As illustrated in FIGS. 3A-3D, with the oral appliance 200 positioned in the mouth and the portion 233 of the attachment member 232 between the front lower teeth, the anchor 230 resides between the user's teeth and the user's lower lip 406, lying flat against the teeth with portion 233 spaced from the gum, limiting the portion 233 from resting on the gum and causing irritation. The mandible 408, epiglottis 410, uvula 412, and soft palate 414 are also shown in FIG. 3D for reference. As can be seen in FIG. 3D, the user has extended their tongue forward in their mouth such that the distal tip (front portion) of the tongue is outside of the front teeth and the oral appliance 200 is holding the tongue forward while the patient is sleeping to prevent the back of the tongue from contacting the uvula and back of the throat to prevent apnea and/or snoring. The distal tip of the tongue and the portion of the tongue in front of the tongue retention elements are at rest while the pharyngeal portion of the tongue remains tensioned and advanced.

Referring again to FIGS. 1 and 2A-2C, in one embodiment the tongue engagement element 204 includes a tensioning mechanism 236 that aids in securing the tongue engagement element 204 in the user's mouth by keeping the portion 233 of the attachment member 232 under tension and thus keeping anchor 230 in place against the front of the user's lower teeth and gum. The tensioning mechanism 236 also provides some flexibility in the length of portion 233 between the frame 205 and the anchor 230, which helps accommodate varying dimensions of lower front incisors. To form the tensioning mechanism 236, the front region 206 of the tongue engagement element 204 includes a raised bridge to which one end of the attachment member 232 is secured. When the anchor 230 is pulled, the bridge 236 is resiliently deformed, placing the portion 233 of the attachment member 232 under tension. The other end of the attachment member 232 is secured to one of the side regions 210, 212.

Figure 7:
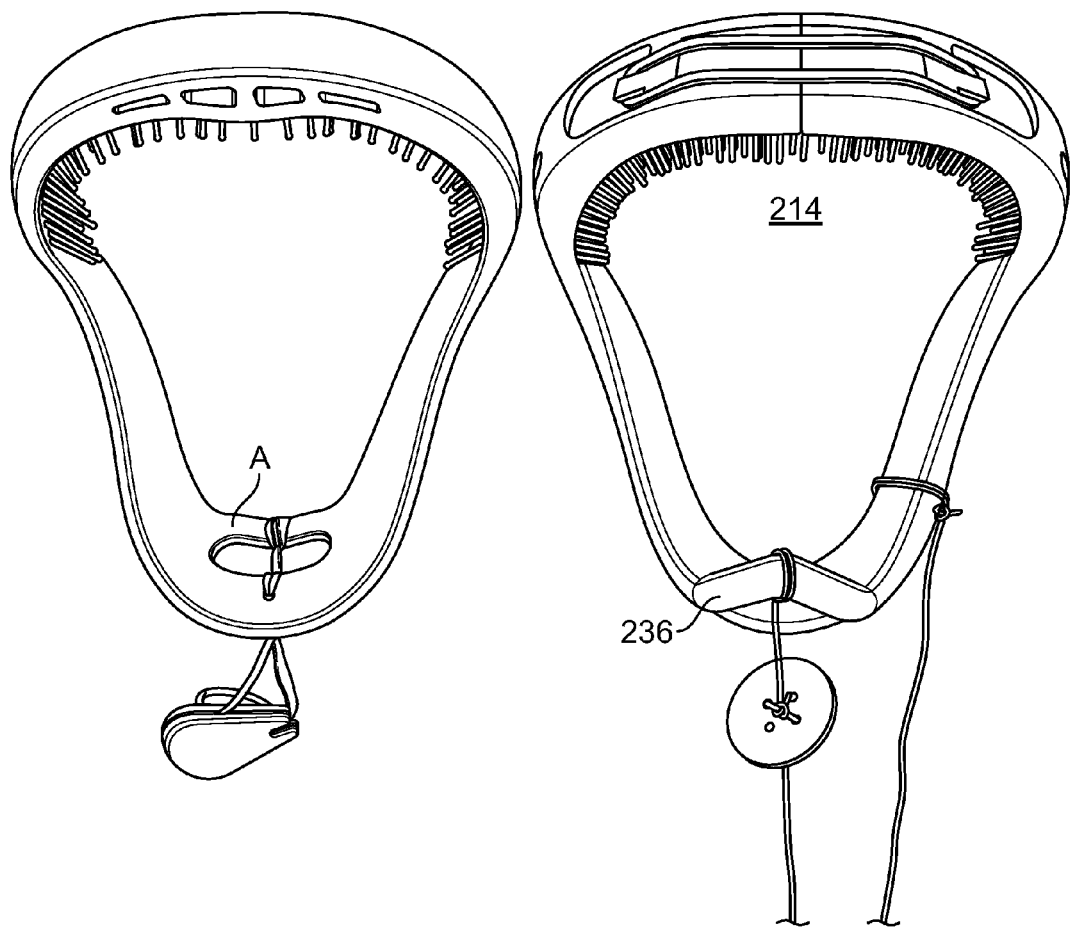
FIG. 7 is a side-by-side comparison of two embodiments of oral appliances.

Referring to FIG. 7, as compared to the tensioning mechanism A of the tongue engagement element embodiment of FIGS. 27A-27D of PCT Publication No. WO 2011/156396, supra, the stacked placement of the tensioning mechanism 236 provides an enlarged opening 214 providing increased space for the user's frenulum.

Figure 8A:
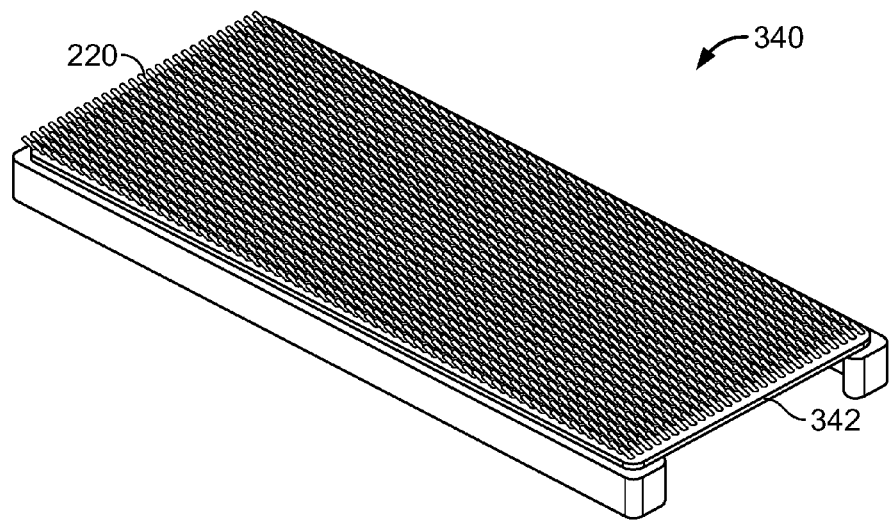
FIG. 8A is an isometric view of tongue engaging structures of one embodiment of the oral appliance in the form of bristles.
Figure 8B:
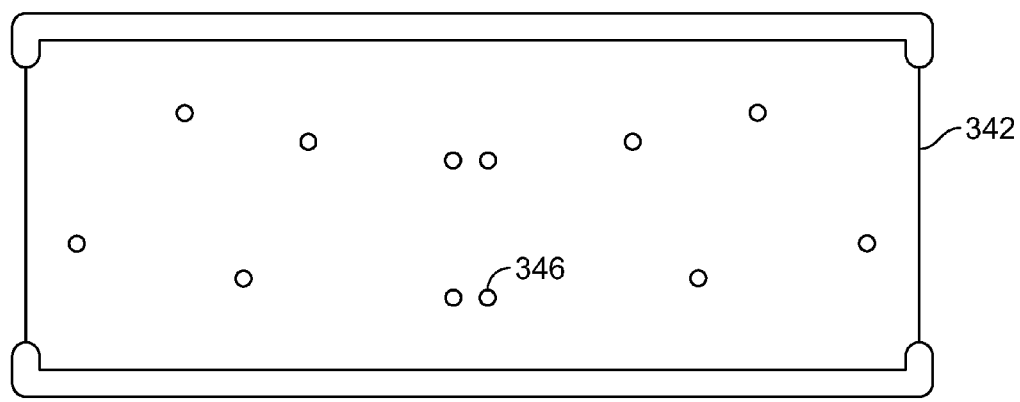
FIG. 8B is a bottom view of the bristles of FIG. 8A.
Figure 8C:
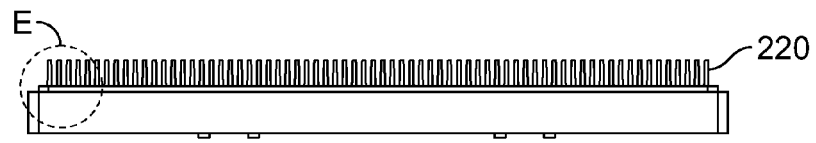
FIG. 8C is a front view of the bristles of FIG. 8A.
Figure 8D:
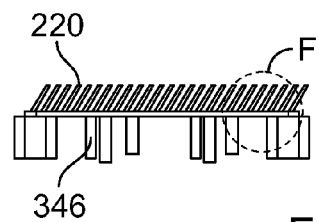
FIG. 8D is a lateral view of the bristles of FIG. 8A.
Figure 8E:
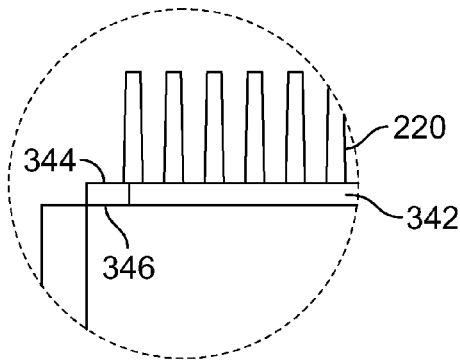
FIG. 8E is a close-up view of portion E of FIG. 8C.
Figure 8F:
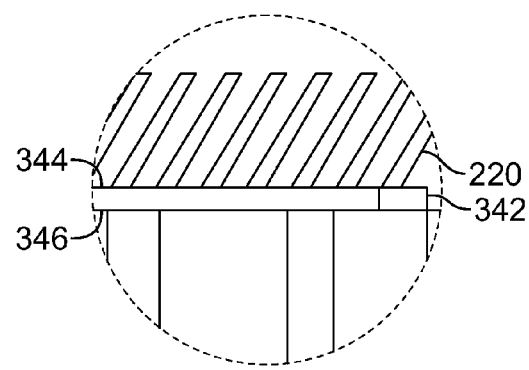
FIG. 8F is a close-up view of portion F of FIG. 8D.
Figure 8G:
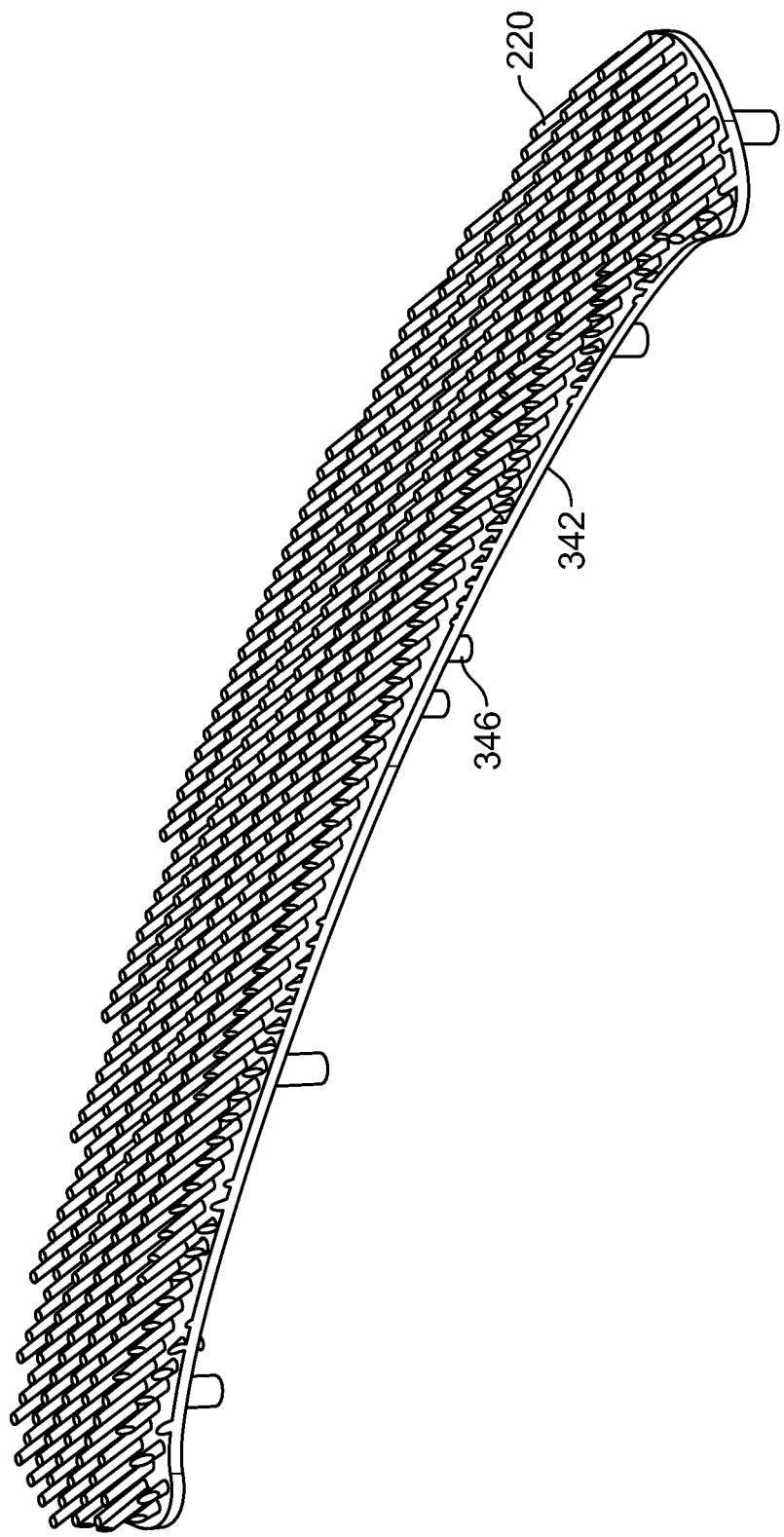
FIG. 8G is an isometric view of the bristles of FIG. 8A.

Referring to FIGS. 8A-8F, in one embodiment the tongue retention system 220 is preferably formed by bristles having selected height, angle and density to provide the needed comfort for the user to wear the oral appliance 200 through the night while also retaining the tongue forward in the mouth as the user sleeps or exercises. For user comfort and grip, the bristles 220 are at an angle to the surface of the tongue (and inner surface of the tongue engagement element 204) and can bend to lie flat between the user's tongue and the inside surfaces 218, 222, 224 of the rear region 208 when the tongue engagement element 204 is positioned on the user's tongue. Any backward motion of the tongue relative to the tongue engagement element 204 causes the bristles 220 to flex downward and engage the tongue to resist the backward motion of the tongue. The bristles 220 are molded in sheet form 340 with a base 342. The bristles 220 extend from a first face 344 of the base 342, and posts 346 extend from a bonding face 348 of the base 342. The posts 346 are used for registration in cutting and bonding the sheet form 340. A cut sheet ready for attachment to the frame 205 is shown in FIG. 8G. Alternatively, the bristles 220 can be molded in the final geometry to eliminate the need to cut the shape from the sheet. The bristles 220 can also be insert molded or co-molded directly on the frame 205. The bristles, frame, anchor, pull tab and attachment member can be one complete molded part rather than being separate parts assembled together.

Examples of dimensions and material properties of base 342 and bristles 220 are:

Total height of base and micro-bristles: 3 mm–1 mm/+2 mm

Base thickness: 0.5 mm–0.25 mm/+0.5 mm

Bristle height (measured vertically from top of base): 2.5 mm–1 mm/+2 mm

Bristle angle (measured from vertical): 30°–15°/+30°

Bristle density: 122/cm$^2$–60/+30

Bristle diameter at tip: 0.3 mm–0.1 mm/+0.2 mm

Bristle diameter at base: 0.44 mm–0.1 mm/+0.2 mm

Spacing between bristles at base: 0.5 mm–0.1 mm/+0.2 mm

Material: 70-90 Shore A or 30-50 Shore D, for example, TEXIN 70 Shore A or PEBAX 40 Shore D.

In a preferred embodiment, the diameter of the bristles 220 is sized to fit within the papillae. Furthermore, in a preferred embodiment, the bristles 220 are dimensioned and formed of a material, for example, Texin, to have sufficient stiffness to resist prolapsing when subjected to a force by the weight of the tongue when the user is supine, but the bristles are not completely rigid. Parameters of the bristles can be modified to achieve differences in performance. For example, if a larger fit range is desired, the bristle height can be increased. The grip of the bristles on the tongue can be modified by changing the material stiffness. The shape and size of the tongue-engaging end of the bristles can be selected to affect performance and comfort.

Figure 9:
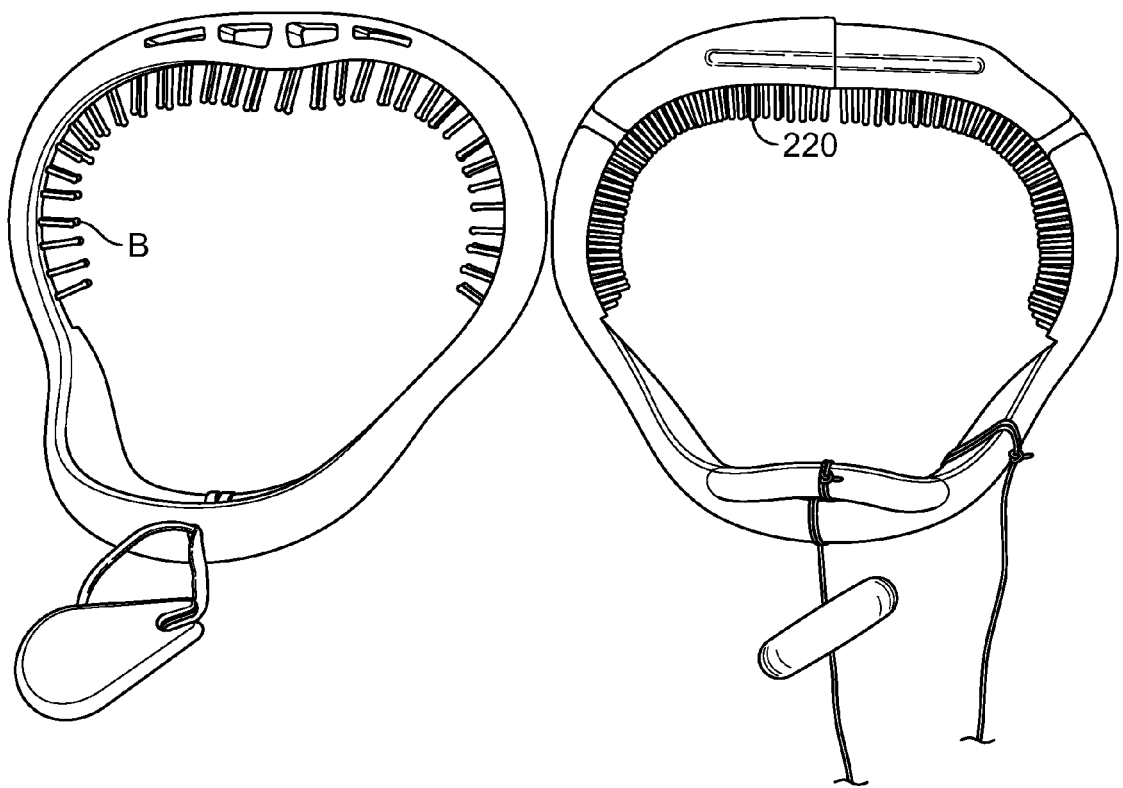
FIG. 9 is a side-by-side comparison of two embodiments of oral appliances.

Referring to FIG. 9, as compared to the bristles B of the tongue engagement element embodiment of FIGS. 27A-27D of PCT Publication No. WO 2011/156396, supra, bristles 220 have a higher density and are molded as a single sheet. The higher bristle density distributes the load across a greater number of points per unit area. This reduces the sensation of sharpness from the bristles (comfort) and increases grip because there are a greater number of engagement points. In a preferred embodiment, the bristles 220 are tapered over their length to form a conical shape such that strain on the bristles is distributed over the length of the bristles rather than being concentrated at the bristle connection to the base 342. This taper also provides a small diameter at the tip to facilitate grip while having a robust geometry at the base. The taper also improves moldability.

Figure 10:
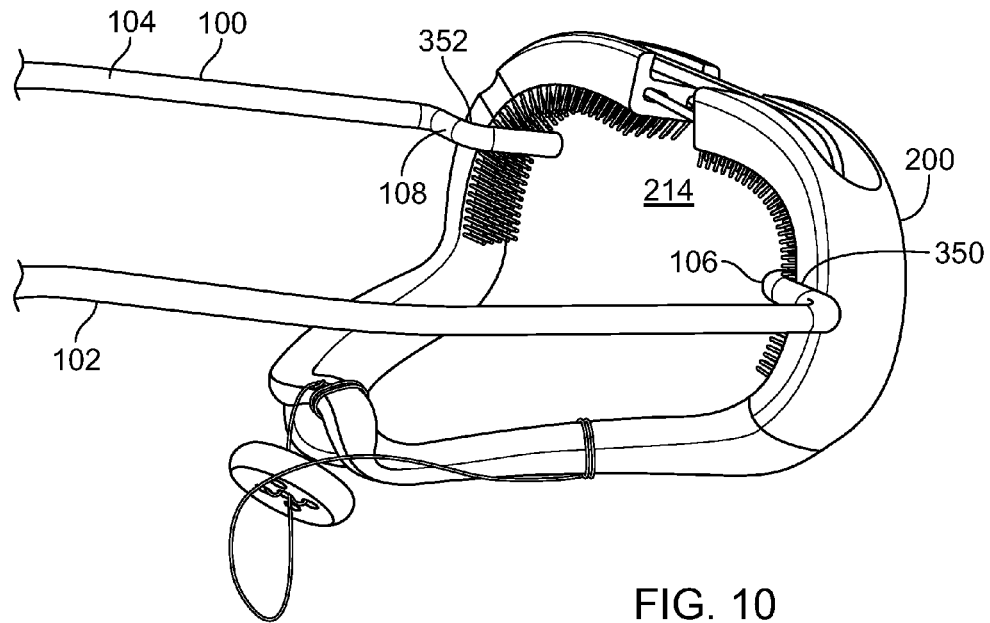
FIG. 10 is another view of one embodiment of the oral appliance expanded by the installation tool.
Figure 11:
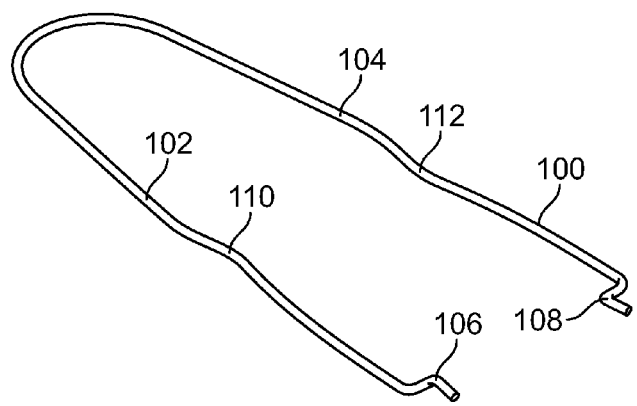
FIG. 11 illustrates the installation tool.

Referring to FIGS. 10 and 11, the user can employ the installation tool 100 to aid in placing the oral appliance 200 on their tongue. The installation tool 100 is generally U or V-shaped with two arms 102, 104 each with an end prong 106, 108. The arms 102, 104 can be squeezed together to fit the end prongs 106, 108 within opening 214. Upon release of the arms 102, 104, the inserter 100 engages and expands the tongue engagement element 204. The tongue engagement element 204 defines notches 350, 352 (see also FIG. 2A) that receive the end prongs 106, 108. The installation tool 100 has recessed curves 110, 112 on the sides to guide the user's hand position. The length of the installation tool 100 is designed to position the hand at least 1 inch from the mouth when inserting the tongue engagement element 204 so the hand position does not block visibility of the frame 205. The diameter and tip gap of the installation tool 100 are designed to provide sufficient opening force to expand all size tongue engagement elements maximally.

Figure 12A:
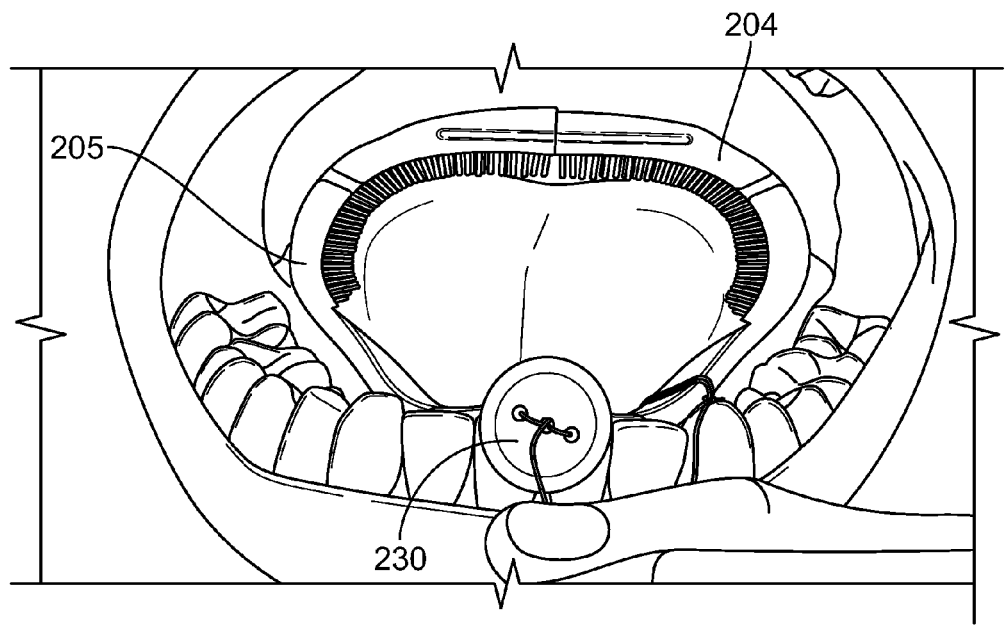
FIGS. 12A, 12B, and 13 illustrate steps in the insertion of an oral appliance in a user's mouth without use of an installation tool.
Figure 12B:
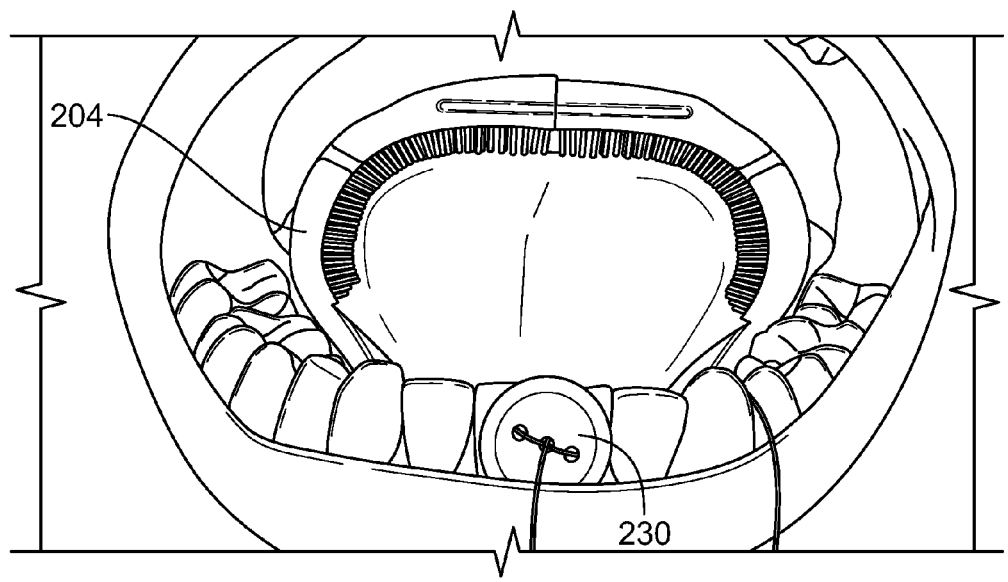
Figure 13:
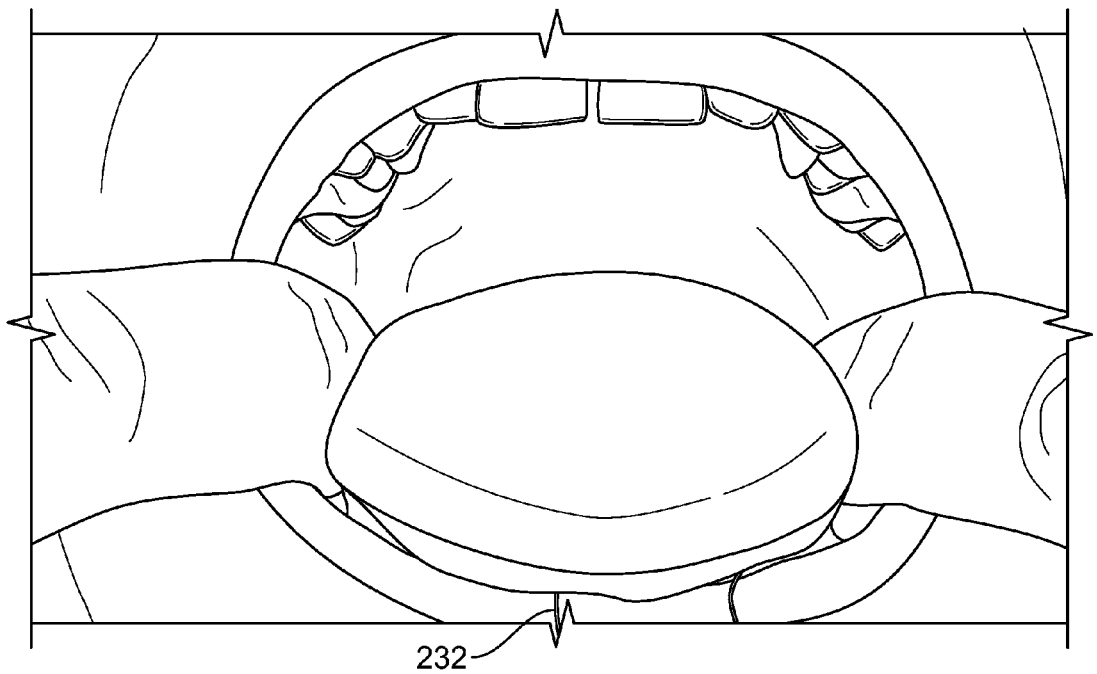
Figure 14:
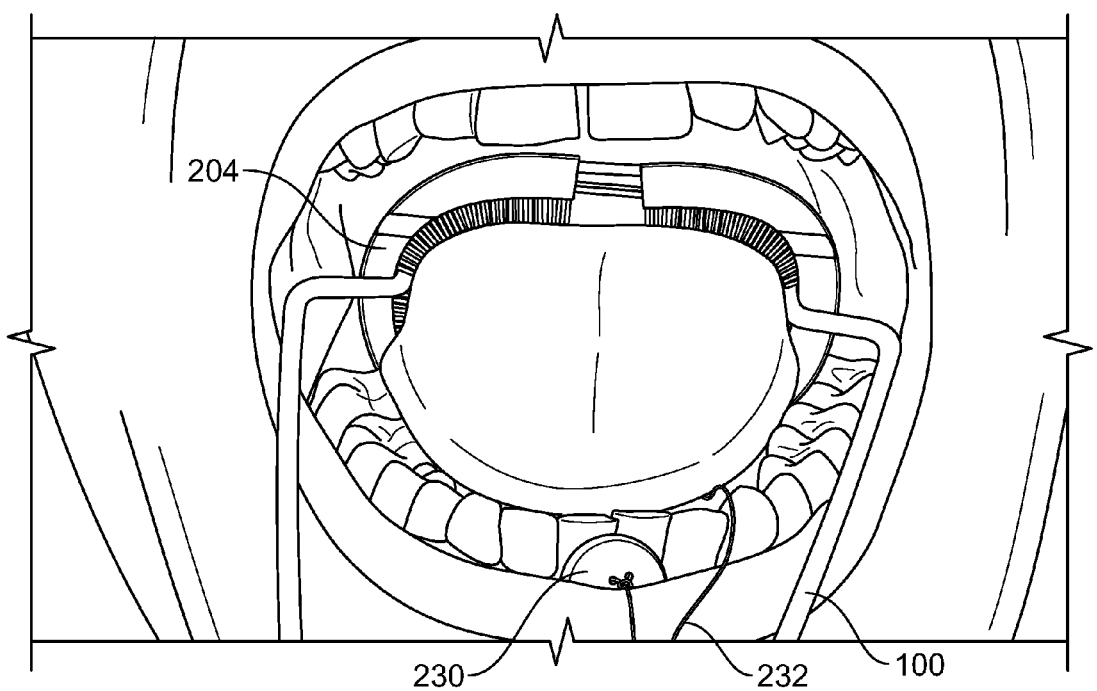
FIG. 14 illustrates insertion of the oral appliance in a user's mouth with use of an installation tool.
Figure 15:
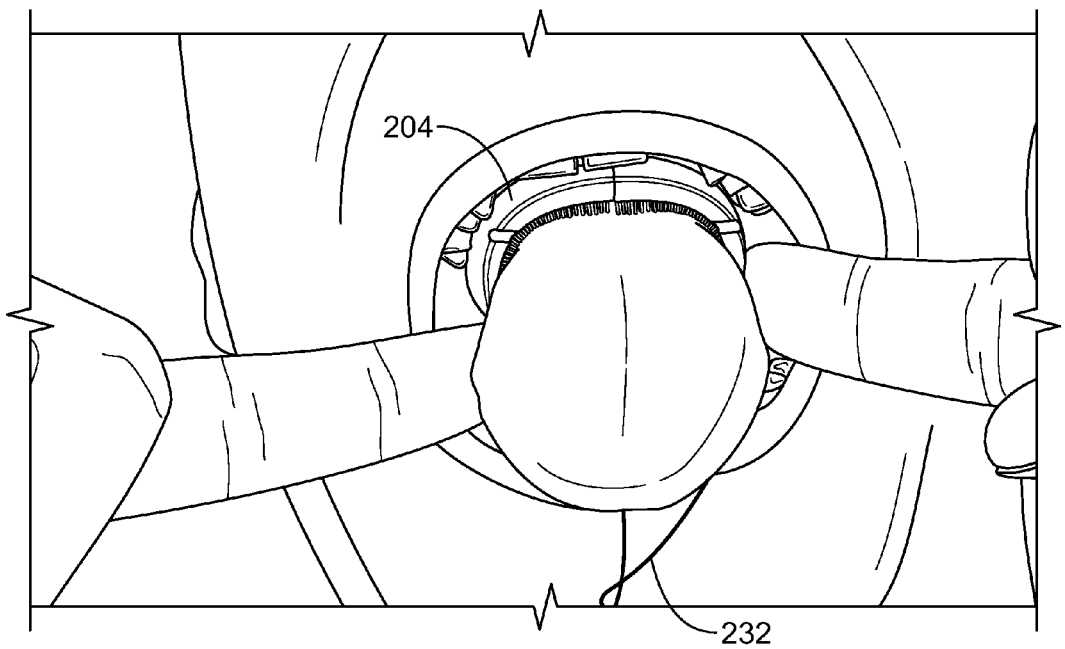
FIG. 15 illustrates removal of an oral appliance.
Figure 16:
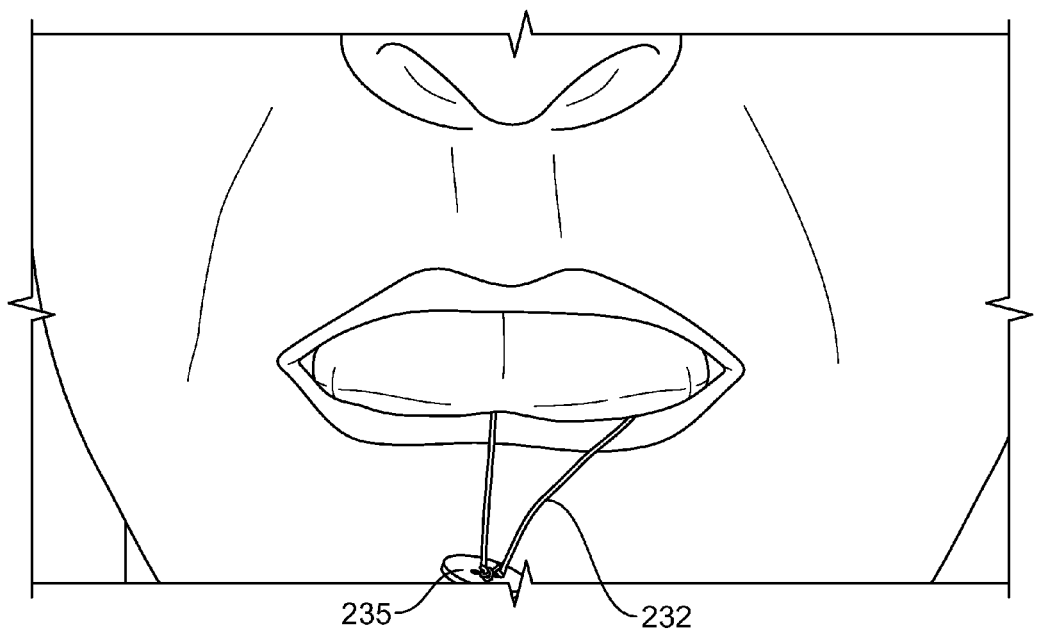
FIGS. 16 and 17 illustrate a user after insertion of the oral appliance.
Figure 17:
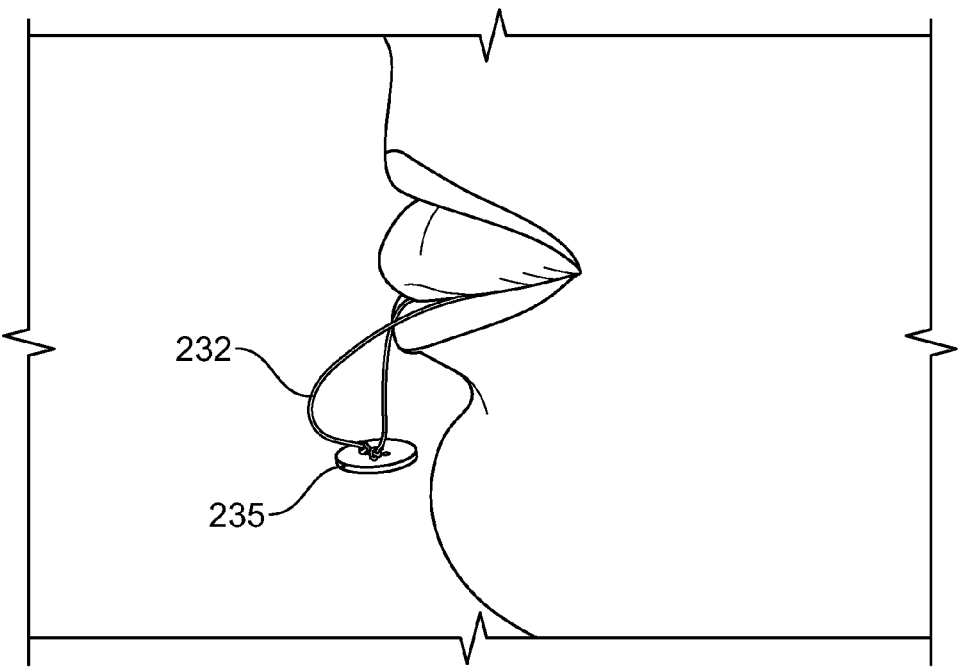

To place and secure the oral appliance 200, in one embodiment, the user places the tongue engagement element 204 into their mouth without inserting their tongue into the frame 205 (FIG. 12A), and grasps the pull tab 235 and uses the pull tab 235 to maneuver the portion 233 of the attachment member 232 between their two front lower teeth with the anchor 230 between the front surface of the front lower teeth and the inside of the lower lip (FIG. 12B). The attachment member 232 can be positioned between the two front lower teeth by pulling down on the tab 235 outside the mouth or by using a finger to push down on the frame 205 just behind the teeth while pulling down on the tab 235 outside the mouth. By hand (FIG. 13) or using the installation tool 100 (FIG. 14) the user expands the tongue engagement element 204 and slides the tongue engagement element 204 back into their mouth while extending their tongue or pulling the tongue with the tongue engagement element 204 under a front region of a tongue and over a rear region of the tongue with the side regions 210, 212 of the tongue engagement element 204 extending along the floor of the user's mouth cavity under the tongue. The user releases their fingers or the installation tool allowing the tongue engaging element to move toward its unexpanded position and engage the user's tongue (FIG. 15). The pull tab 235 remains outside the user's mouth and the user extends their tongue forward to position the tip at or in front of the lips to open the airway as much as is comfortably possible (FIGS. 16 and 17).

It is not necessary to expand the frame for installation although it does make it easier. The angle of the bristles allows the tongue to be inserted even without expansion. Further, the mechanism allows the frame to expand dynamically if the tongue requires some space during installation.

After sleeping with the oral appliance 200, to remove the oral appliance, the user releases the oral appliance using their fingers to lift the frame 205 off their tongue as shown in FIG. 15, and then retracts their tongue from within the frame. The user then releases the portion 233 of the attachment member 232 by grasping the pull tab 235 and pulling in an upward direction. This releases the portion 233 from between the two front teeth. The user uses the pull tab 235 to pull the appliance forward out of their mouth.

In a preferred embodiment, the bristles 220 contact the user's tongue at or behind the second molars #18, 31 and in front of the pharyngeal reflex in a zone in the back of the tongue corresponding to the last row of molars (the wisdom teeth). The bristles 220 engaging the tongue act to resist rearward motion of the tongue. The tongue engagement element 204 fits within the lingual surfaces of the teeth with an attachment below the bite contacting surfaces of the lower teeth. The tongue engagement element 204 thus positioned does not interfere with the user's normal bite.

The bridge 236 typically deforms to provide enough length of the portion 233 between the anchor 230 and the front region 206 of the tongue engagement element 204 to allow the portion 233 to be positioned between the front middle teeth, and the anchor 230 to be positioned in front of the teeth. Typically some deformity of the bridge 238 remains to maintain tension on the portion 233 and to accommodate various thicknesses of different user's teeth. For example, if the front two teeth of a user are overlapped such that one tooth is sticking farther forward, for example, 2 mm, the bridge will be deflected toward the teeth by 2 mm so as to provide 2 mm more of floss length to accommodate the greater thickness as compared to a user who has straight teeth.

Figure 18A:
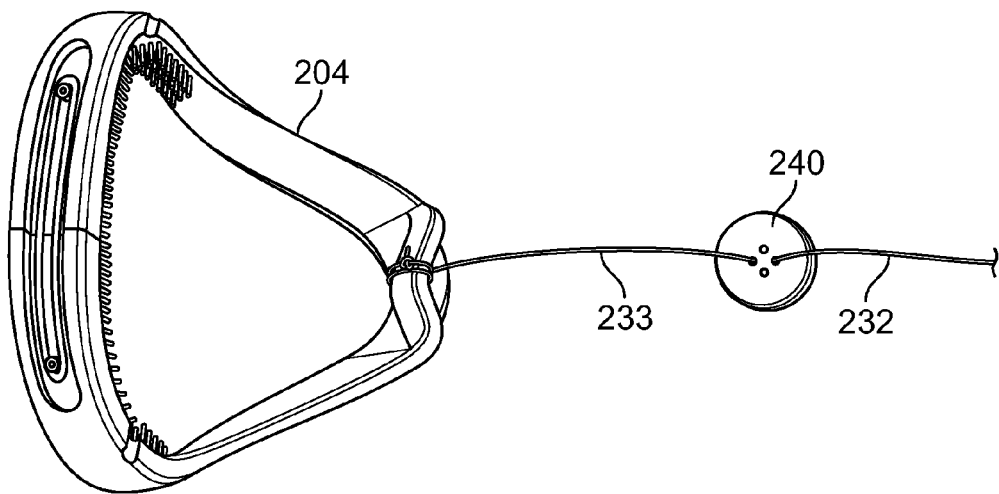
FIGS. 18A-18E show the steps for attaching an adjustable anchor to the frame of the oral appliance.
Figure 18B:
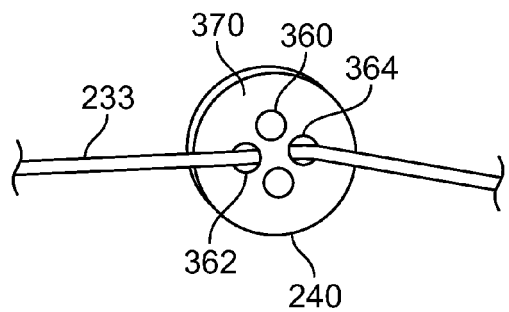
Figure 18C:
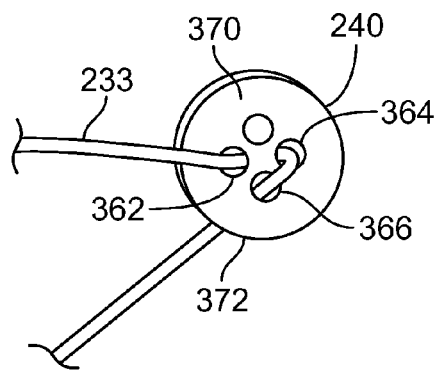
Figure 18D:
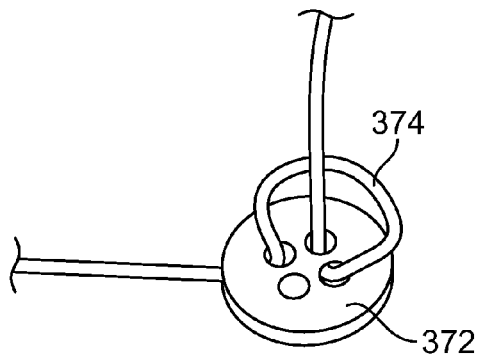
Figure 18E:
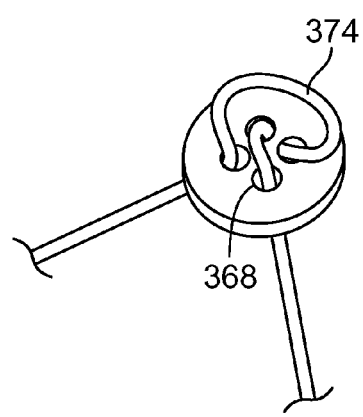
Figure 19:
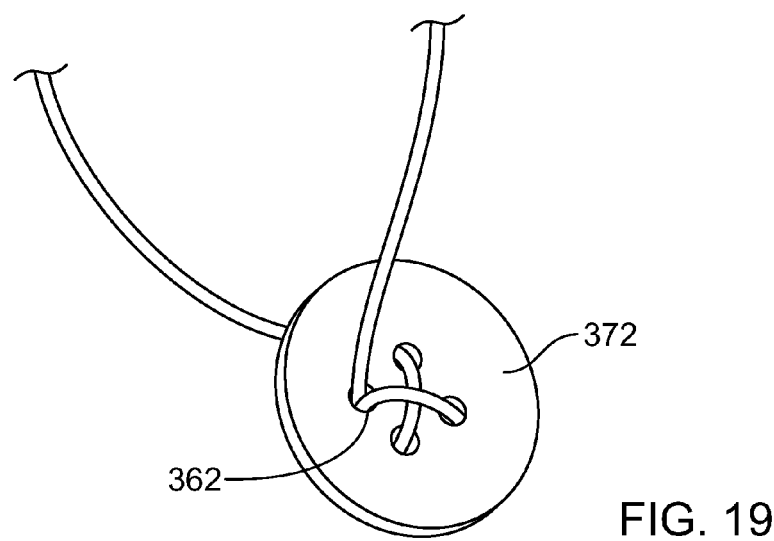
FIG. 19 shows the adjustable anchor of FIGS. 18A-18E attached to the frame.
Figure 20:
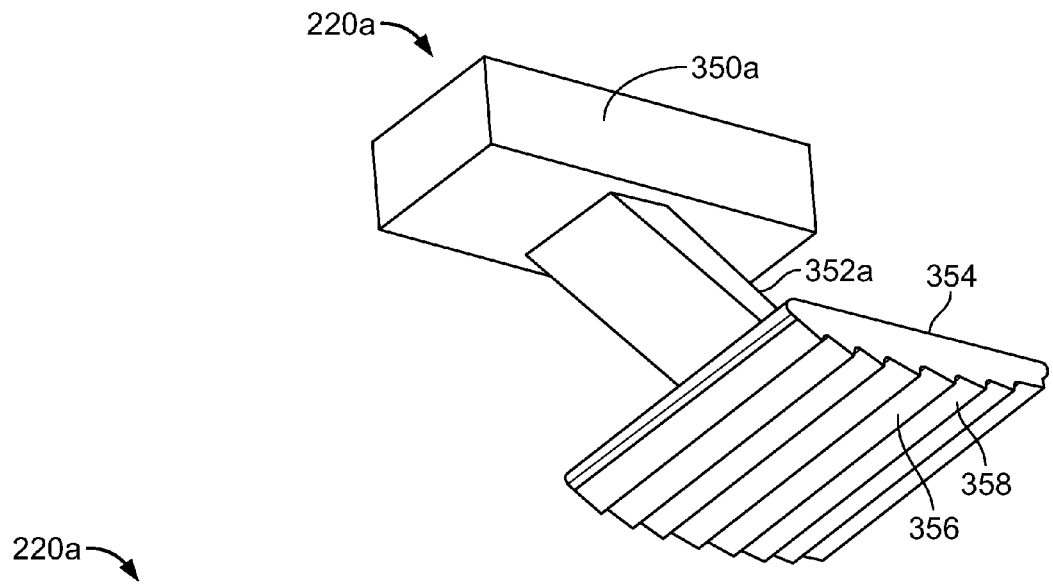
FIGS. 20-23 illustrate an alternative embodiment of tongue engaging structures.
Figure 21:
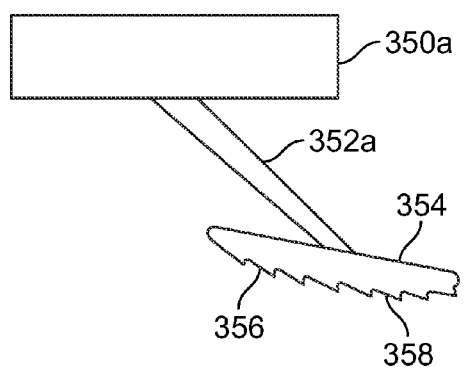

The anchor 230 can be attached to the attachment member 232 in a manner that permits the length of portion 233 to be adjusted enabling tightening of the frame against the teeth. The adjustable anchor can be implemented with a locking mechanism within the anchor or by routing the attachment member 232 through the anchor in a manner that allows adjustment. The mechanism can be implemented with a feature that clamps onto the attachment member and is released with twisting, tension, or compression to overpower the integrated clamp. The attachment member can be routed through the anchor in a fashion that allows tightening and limits loosening. Loosening can be achieved by holding the anchor at an angle relative to the axis of the attachment member. Loosening can also be achieved with an active integrated mechanism that removes the locking pressure from the routing of the attachment member through the anchor Referring to FIGS. 18A-18E, in an illustrated embodiment, the anchor 230 defines four holes 360. The attachment member 232 is thread through a first hole 362 (from side 370) and back through the opposite hole 364 (FIGS. 18A and 18B); thread through an adjacent hole 366 from side 370 to the opposite side 372 (FIG. 18C); after pulling up on the loop 374 on side 372 (FIG. 18D), the free end of the attachment member is thread under the loop 374 and through the opposite hole 368 (FIG. 18E) to side 370; the free end of the attachment member is thread again through hole 362 from side 370 to side 372 (FIG. 19). To shorten portion 233, the user can hold pull tab 235 and pull the anchor 230 toward the tongue engagement element 204.

The maximum width of the oral appliance is related to the spacing between the second molars and is limited by the width of the inside of the mandibular dental arch.

The tongue engagement element 204 can be provided in different sizes to accommodate different sized mouths and tongues. For example, referring particularly to FIGS. 2B and 2C, the height, H1, can be range from about 19 to 24 mm, and the width, W1, can range from about 30 to 37 mm, depending on the size of the user's mouth and tongue. The tongue engagement element 204 has a length, L1, for example, of 41.7 cm, which is greater than the width, W1. While the length, L1, may vary depending on the size of the user's mouth, the length, L1, will generally be greater than the width, W1. The length, L2, of the side regions 210, 212, is, for example, 21.7 mm. The overall width, W2, and height, H2, of the tongue engagement element is, for example, in the range of 35 to 42 mm, and 24 to 29 mm, respectively, and the spacing, H3, between surfaces 216 and 218 is, for example, in the range of 13 to 18 mm. The rear region 208 is, for example, 7.5 mm wide and from 2.5 to 4.5 mm thick. The expansion element 300 can permit, for example, up to about 12 mm of expansion. In a particular embodiment, the body of the appliance is made from PEBAX with a durometer of 55 Shore D, which gives the right balance of stiffness and elasticity. In an alternative embodiment, the material is TEXIN with a durometer of 65 Shore D or Nylon having a similar durometer.

The oral appliance is designed to be too large and too irregularly shaped to substantially obstruct the airway should the oral appliance become dislodged, yet small enough that the user should be able to close his/her mouth completely if desired during use.

Other embodiments are within the scope of the following claims.

Figure 22:
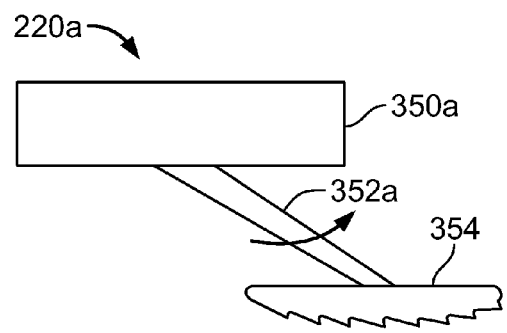
Figure 23:
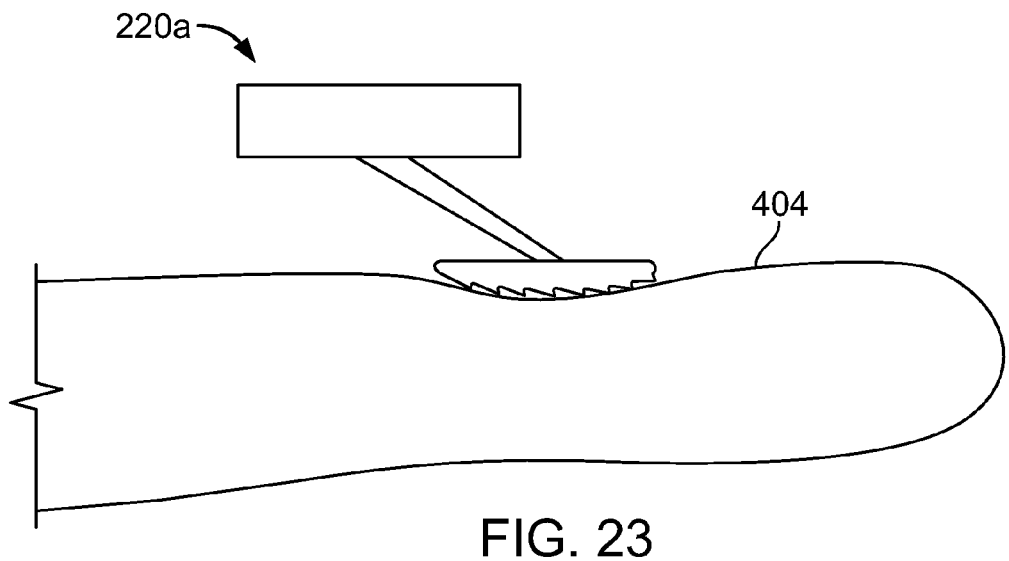

For example, referring to FIGS. 20-23, to aid in comfort, rather than having bristles in direct contact with the tongue, structures 220a that engage the user's tongue include a mount 350a that attaches to the tongue engagement element 204, a bristle 352a attached to the mount 350a, and a pad 354 attached to the bristle 352a. The pad 354 has a surface 356 that contacts the tongue 404. As shown in FIG. 22, the bristle 352a allows the pad 354 to deflect. The pad 354 acts to distribute the loading on the tongue. The tongue contacting surface 356 of the pad 354 can include ridges 358 that aid in allowing the tongue to slide forward while limiting retraction of the tongue. The geometry and material of the bristle 352a can be adjusted to achieve the desired strength in bending, and therefore achieve the desired force that will be applied onto the tongue through the pad 354. The pad's 354 geometry can be adjusted to achieve the desired pressure on the tongue (dependent on the contact area of the pad 354 and the force imparted by the bristle 352a. The pad's 354 geometry can also be adjusted to achieve the desired friction on the tongue (dependent on the contact area and surface texture of the pad 354 and the force imparted by the bristle 352a). Multiple such structures 220a can be mounted on the tongue engagement element. The structures 220a can be injection molded.

Figure 24:
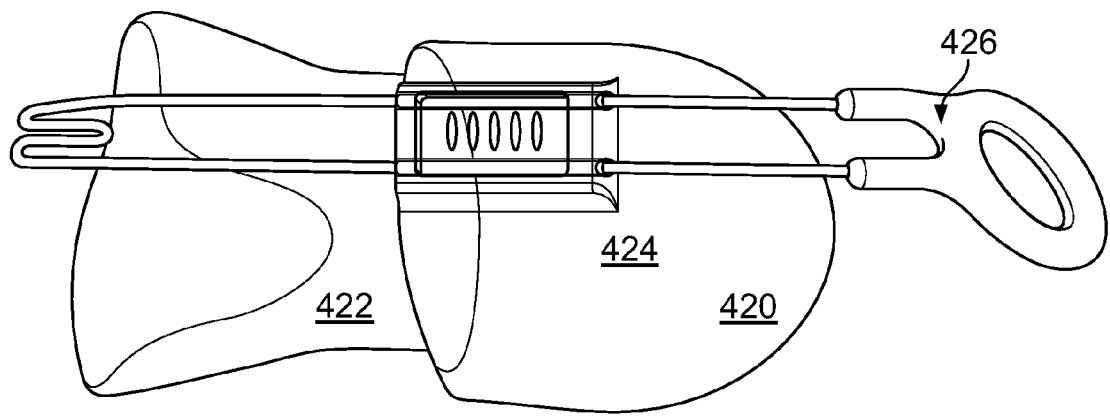
FIGS. 24 and 25 illustrate an alternative embodiment of an installation tool.
Figure 25:
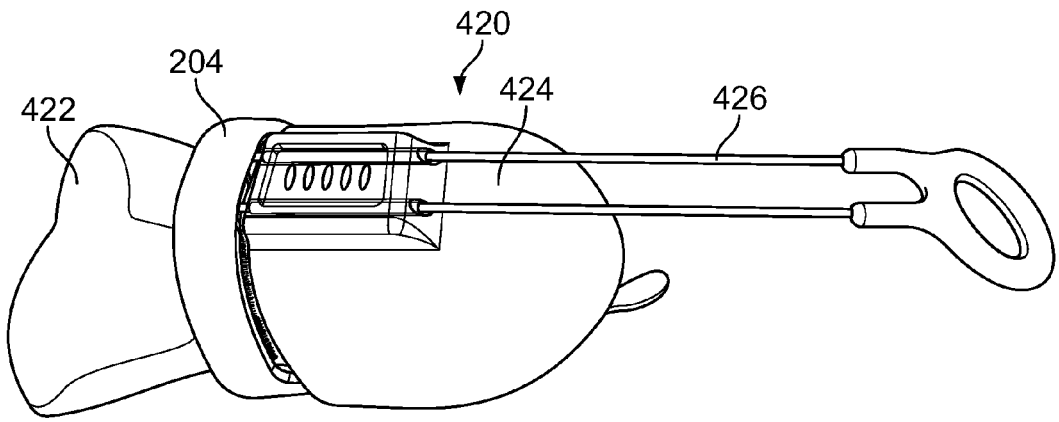

Referring to FIGS. 24 and 25, an alternative installation tool 420 relies on suction to help place the tongue engagement element 204 on the user's tongue. The installation tool 420 includes a tongue receiving frame 422 attached to a bulb 424. Slidably received by the bulb 424 is a pusher member 426. The tongue engagement element 204 is received over the frame 422, which acts to expand the tongue engagement element 204. In use, the user squeezes the bulb 424 and places their tongue in the frame 422. Upon releasing the bulb 424, the installation tool 420 suctions the tongue into the bulb 424. The user then uses the pusher member 426 to slide the tongue engagement element 204 off the frame 422 and onto the tongue. To release the installation tool 420, the user again squeezes the bulb 424 to release the suction and removes the installation tool 420.

In another alternative embodiment of an installation tool similar to installation tool 420, rollers rather than a suction bulb are used to pull the tongue forward. A pair of fabric, for example, gauze covered, rollers replace the suction bulb.

The user places their tongue between the rollers and rotates the rollers to pull their tongue forward between the rollers.

Figure 26A:
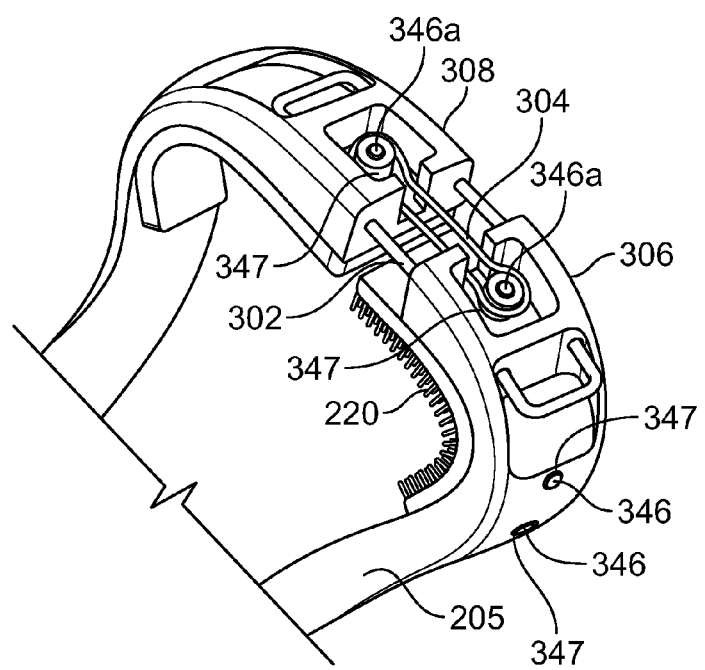
Figure 26B:
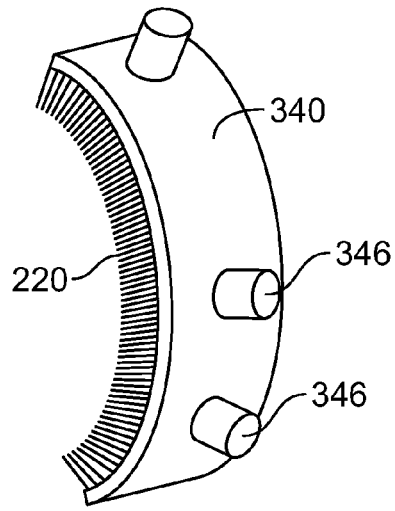
Figure 26C:
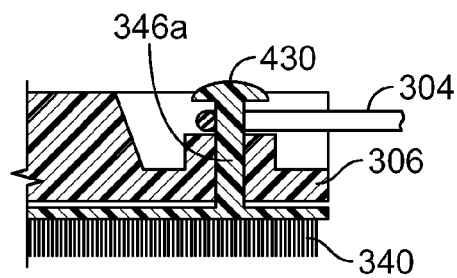
Figure 26D:
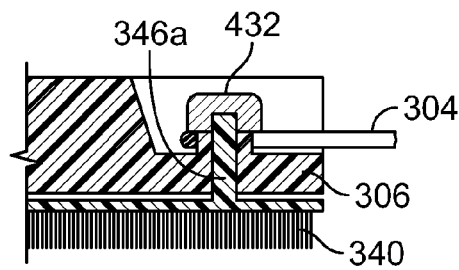
Figure 26E:
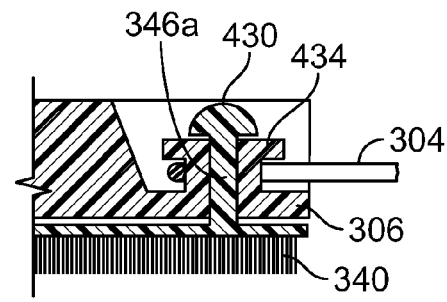

The posts 346 (FIGS. 8B and 8D) can be used to make a mechanical interlock between the frame 205 of the tongue engagement element 204 and the sheet form 340 carrying the bristles 220. Referring to FIGS. 26A and 26B, each part 306, 308 of the frame 205 defines, for example, three holes 347 that each receives one of the posts 346. The biasing member 304 is received around the innermost posts 346a. Three ways of securing the biasing member 304 to the tongue engagement element 204 are illustrated. FIG. 26C shows a heat-staked attachment which forms a head 430 on the post 346a. FIG. 26D shows a cap 432 placed over the post 346a. FIG. 26E shows another heat staked embodiment in which the rubber band 304 is placed below a lip 434 formed in the frame 205.

Figure 27:
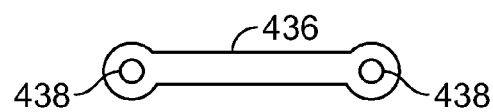
Figure 28A:
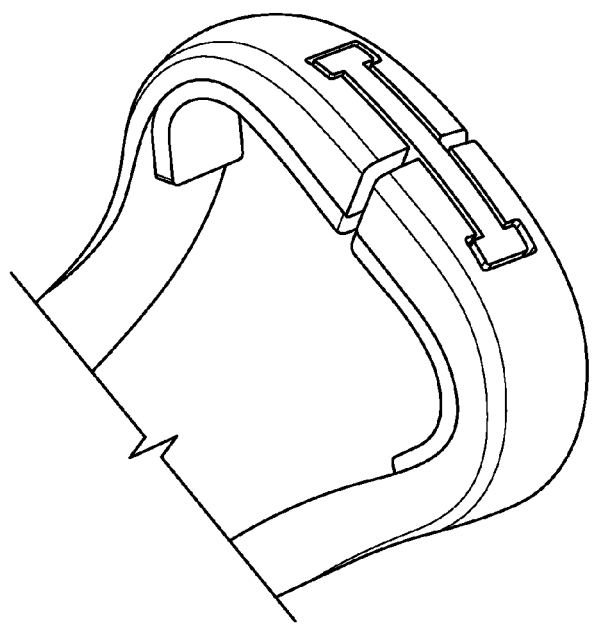
Figure 29:
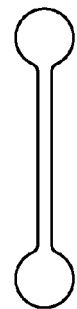
Figure 28B:
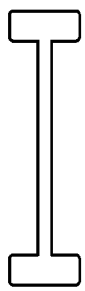

Referring to FIG. 27, rather than an orthodontic elastic, a molded spring 436 defining holes 438 for receiving the posts 346a can be used. FIGS. 28A, 28B, and 29 illustrate other embodiments of elastic or spring material for use as the biasing member 304.

Figure 30A:
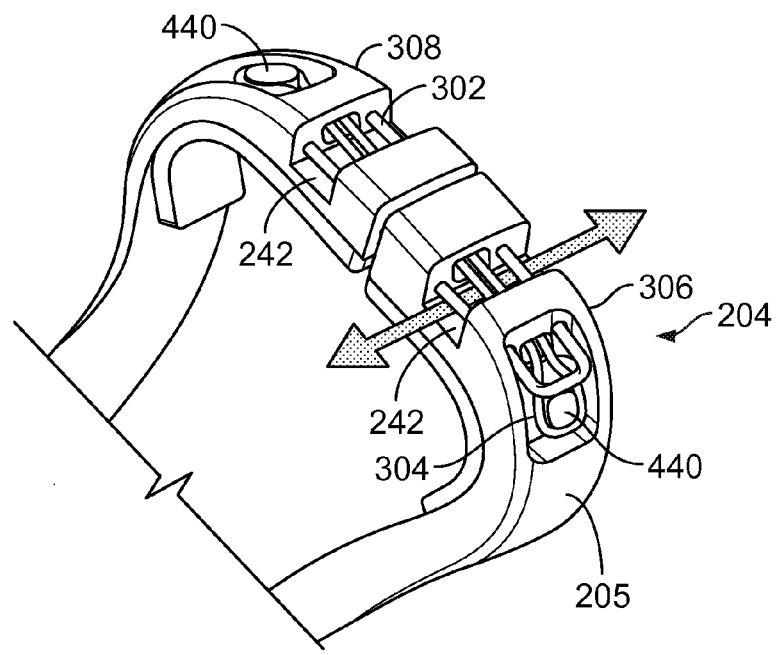
Figure 30B:
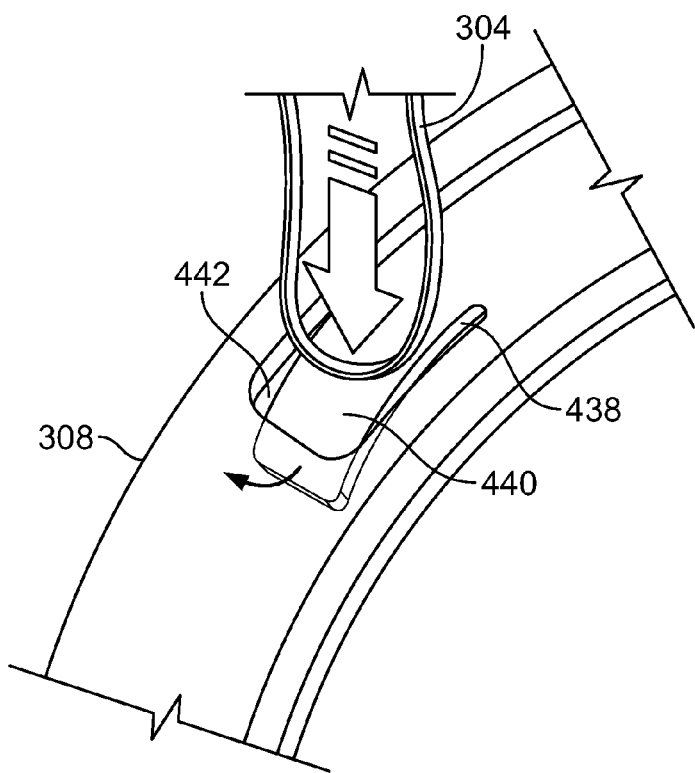
Figure 30C:
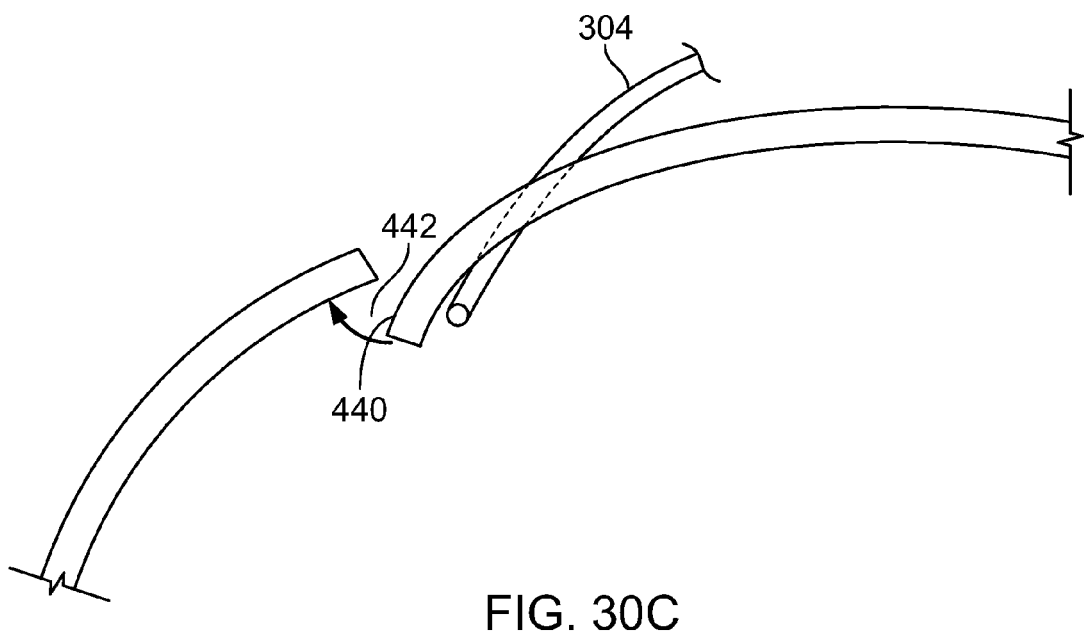

Referring to FIG. 30A-30C, to facilitate air passage through the user's mouth, the tongue engagement element 204 can include air vents 242 extending through the rear region 208. FIGS. 30A-30C also illustrate another way of attaching the biasing member 304 to the frame 205. The frame 205 has a slit 438 in each part 306, 308 that forms a flexible flap 440 under which the biasing member 304 is secured. The flap 440 is pushed down and the biasing member 304 is placed under the flap 440 and extending up through slit 438. When the pushing force is removed, the flap closes off opening 442. The flap 440 is recessed within the frame 205 so that the flap 440 does not rub against the roof of the user's mouth.

Figure 31:
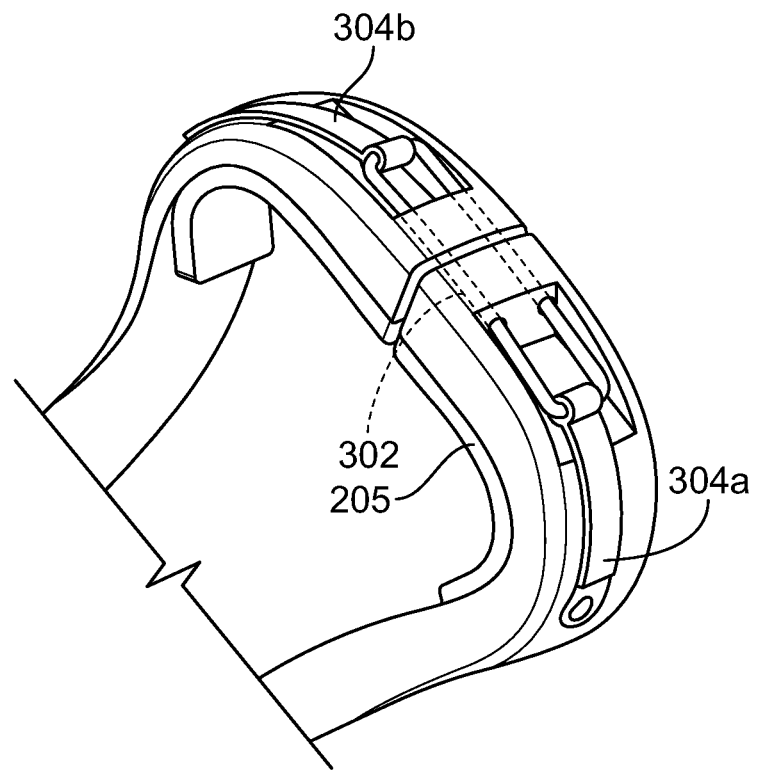

Additional embodiments of the expansion element are illustrated in FIGS. 29-42. For example, referring to FIG. 31, rather than running parallel to the wire guide 302, the biasing member 304, for example, two rubber bands 304a, 304b are attached to the ends of the wire guide 302. The rubber bands 304a, 304b can be heat-staked to the frame 205.

Figure 32:
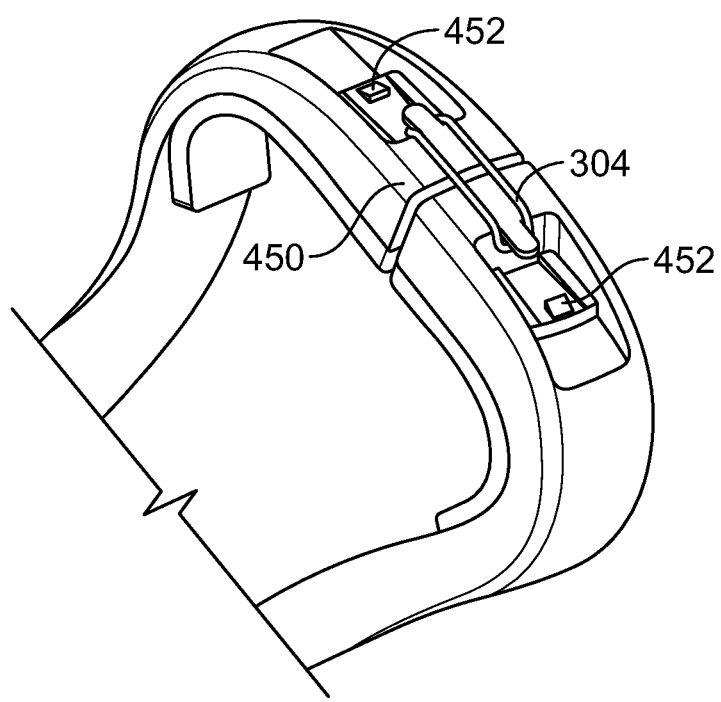
Figure 33:
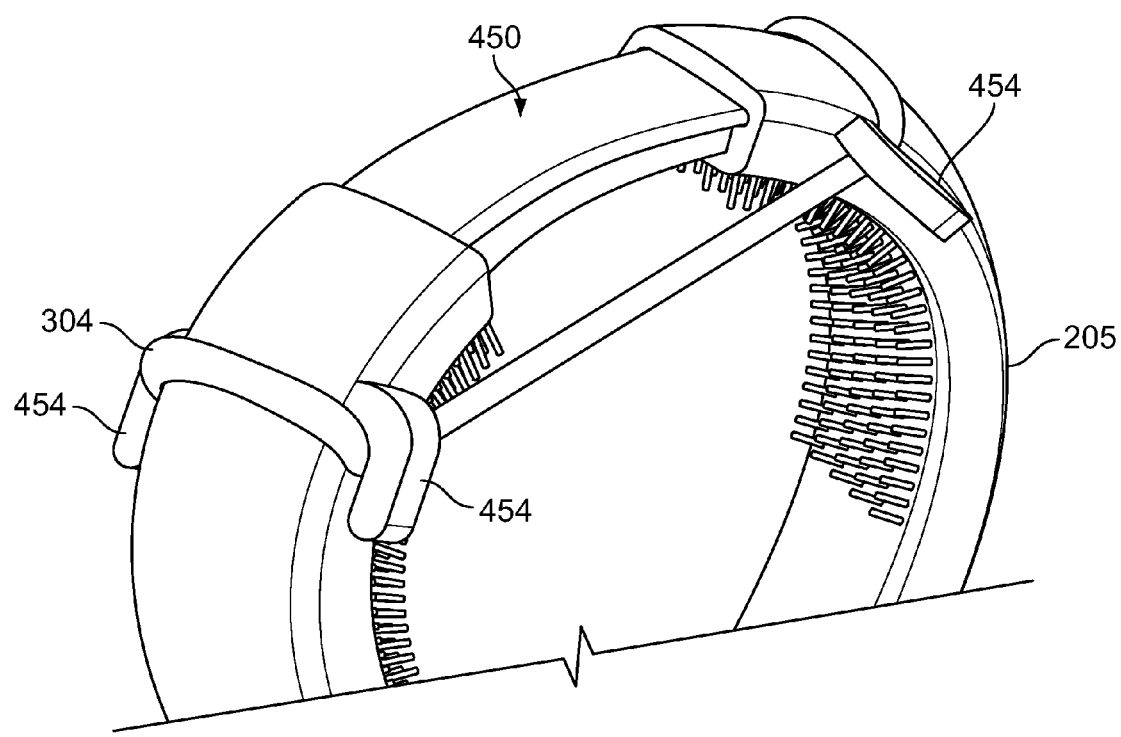
Figure 34A:
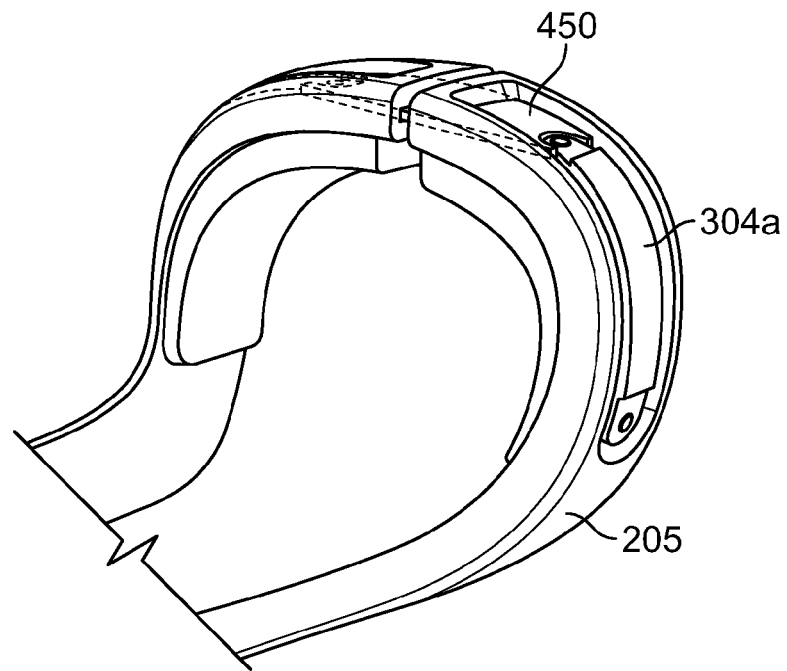
Figure 34B:
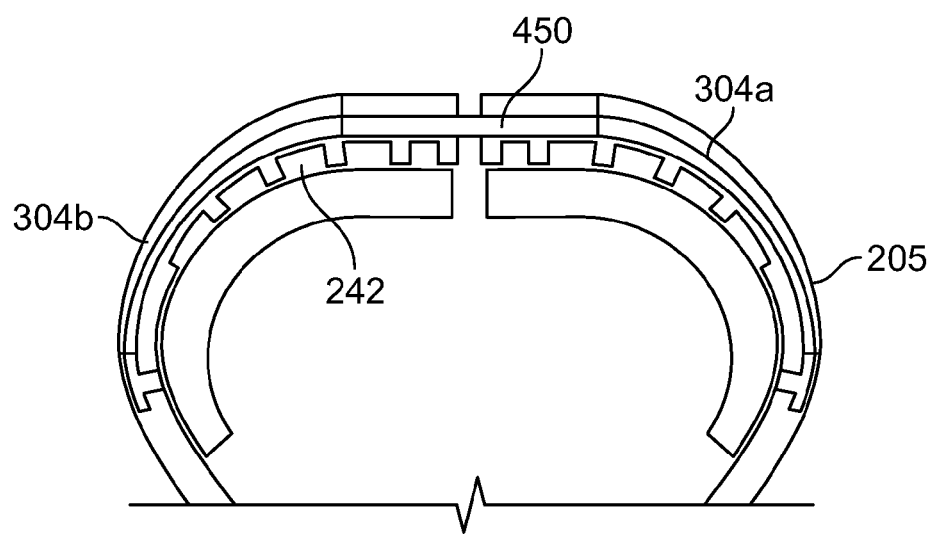

Referring to FIG. 32, rather than a wire guide 302, the expansion element includes a connector 450 along which the tongue engagement element expands, and stop 452 at the ends of the connector that limit the amount the tongue engagement element can expand. As illustrated in FIG. 33, the biasing member 304 can be externally mounted to the frame 205 by, for example, prongs 454. The connector 450 can have curved ends over which the frame 205 is received to assembly the frame 205 to the connector 450. Referring to FIGS. 34A and 34B, the connector 450 can be used with two biasing members 304a, 304b. The frame 205 can define air vents 242.

Figure 35A:
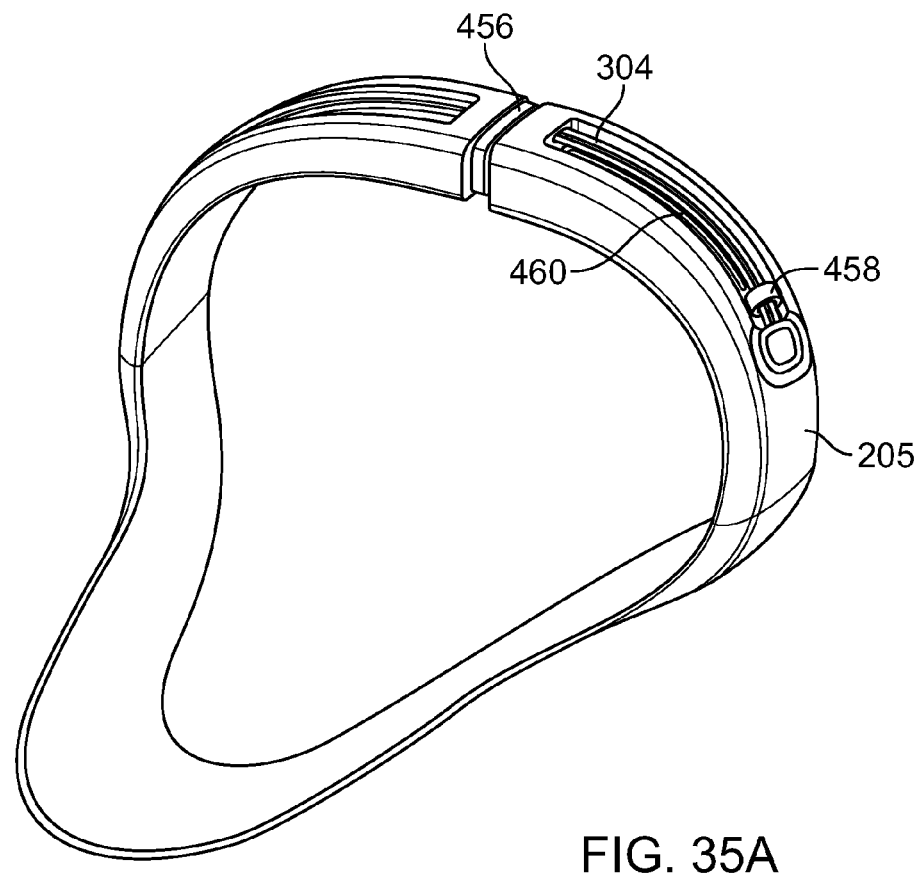
Figure 35B:
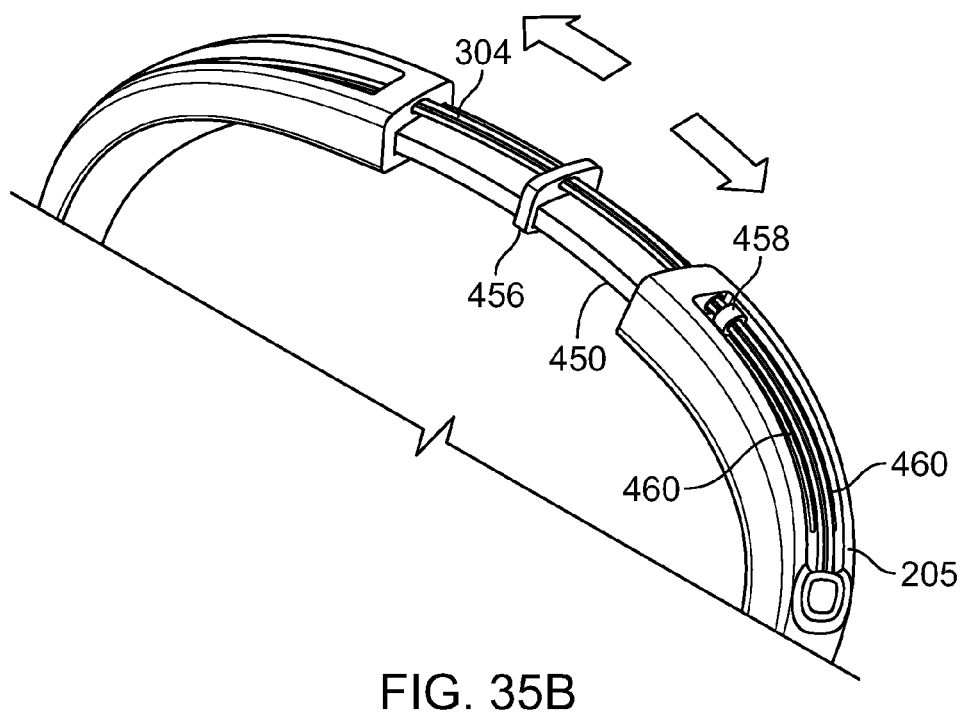
Figure 36B:
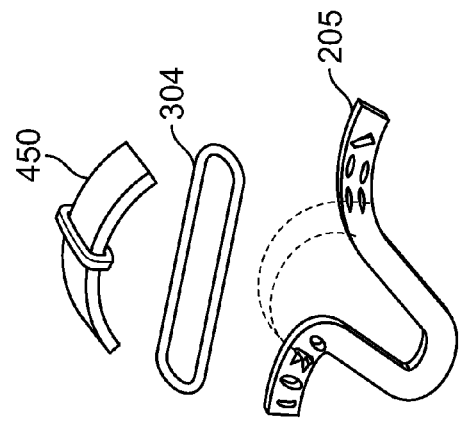
Figure 36A:
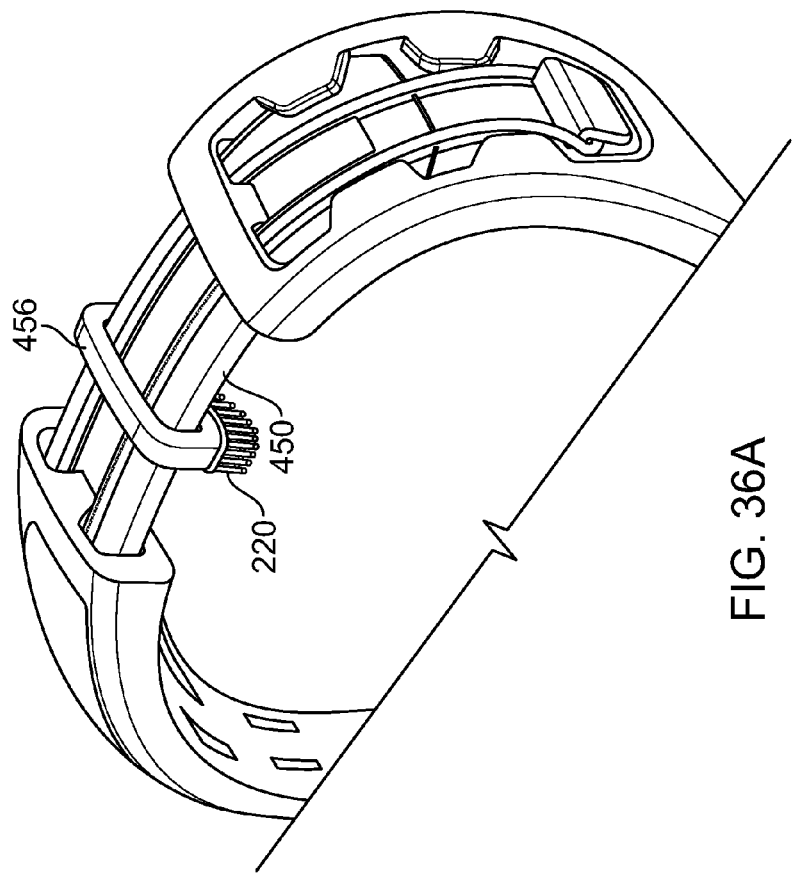

According to the embodiment of FIGS. 35A, 35B, a connector 450 includes a biasing member guide 456 that is molded on the connector 450. The biasing member 304 is located on top of the connector 450 and through the biasing member guide 456. In this embodiment, the connector 450 curves down the sides of the frame 205. The connector includes stabilizers 458, and the frame defines slits 460 within which the stabilizers 458 slide. In the embodiment of FIG. 36A, the biasing member guide 456 includes bristles 220. If the frame 205 is maximally expanded, the bristles 220 on the biasing member guide 456 maintain grip on the tongue in the central region of the frame. As shown in FIG. 36B, to assemble the tongue engagement element, the frame 205 can be molded flat, its sides curled up, and the connector 450 and biasing member 304 slid into place. The user or the manufacturer can select a biasing member 304 that provides a loose, medium, or firm version of the oral appliance 200.

Figure 38:
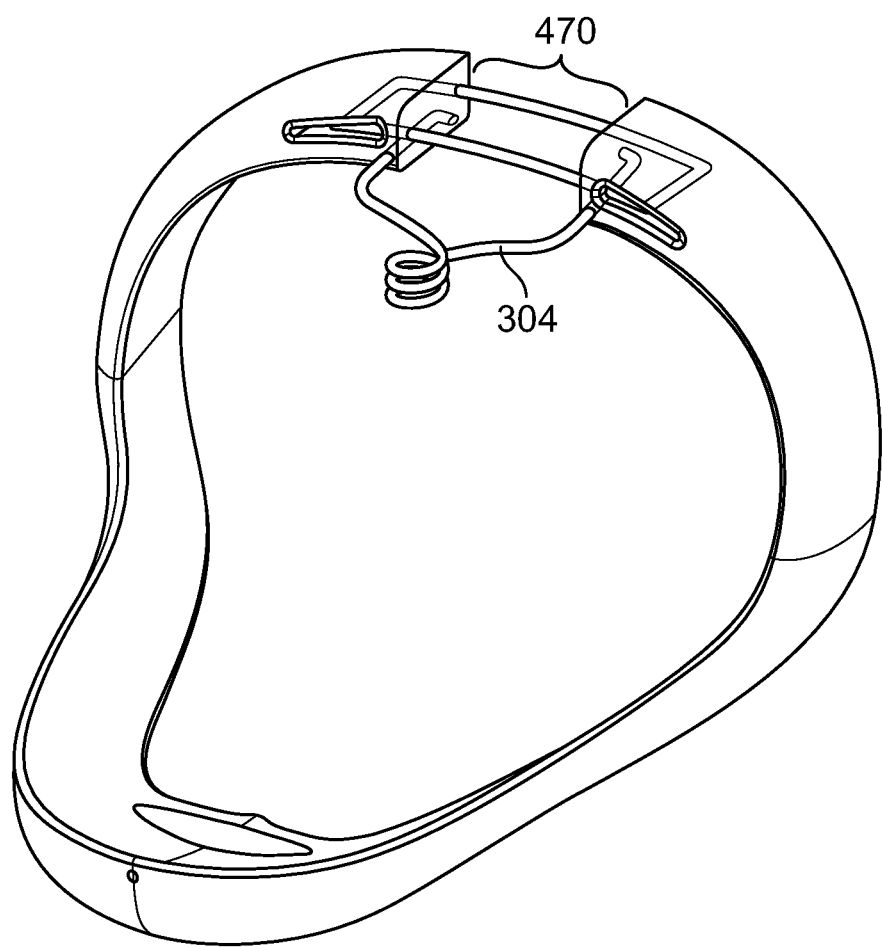
Figure 39:
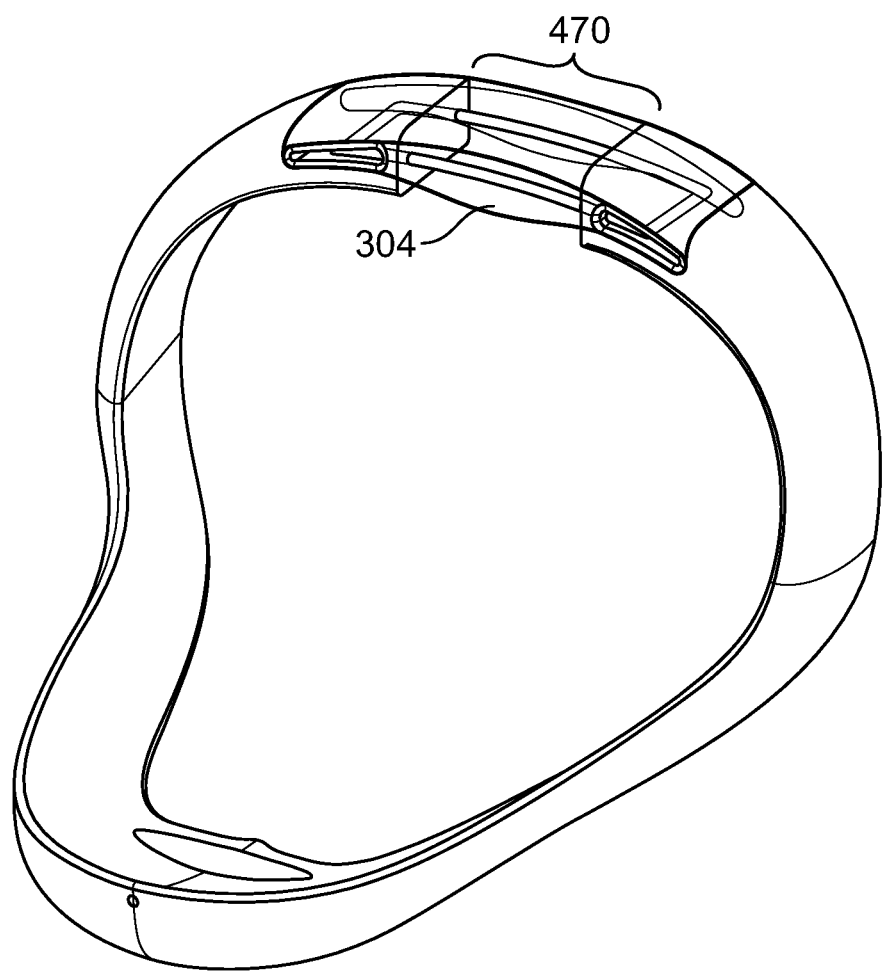

In the embodiment of FIGS. 37A-37D, rather than being split, the frame 205 has a larger gap 470 between parts 306, 308. The gap 470 provides an air vent. The connector 450 spans the gap 470. The connector 450 includes rails 472 that retain the biasing member 304. The connector 450 also defines air vents 242. Additional embodiments with a larger gap 470 are shown in FIGS. 38 and 39. Rather than being an orthodontic elastic, the biasing member 304 in the embodiment of FIG. 38 is a torsion spring and in the embodiment of FIG. 39 is a wide, flat elastic band.

Figure 40B:
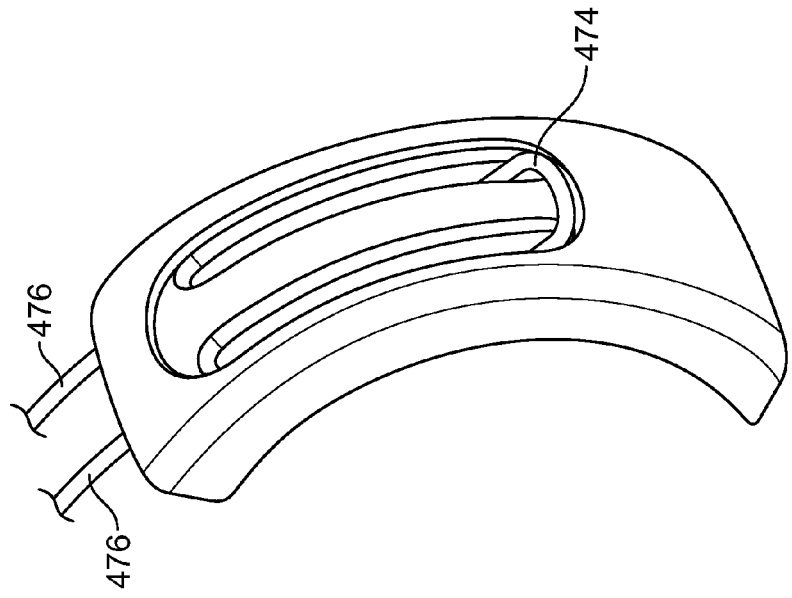
Figure 40A:
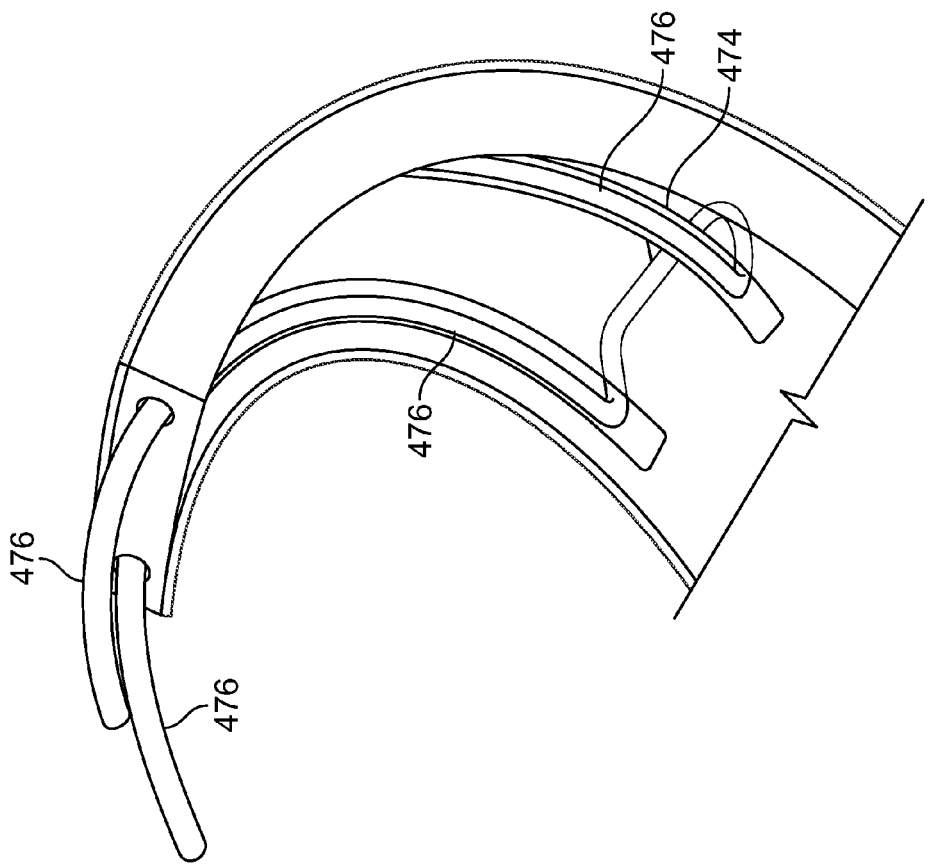

The wire guide 302 and the biasing member 304 can be replaced by a single nitinol or stainless steel wire 474 (FIGS. 40A and 40B). Alternatively, the wire 474 can be used in conjunction with a biasing member 304. The wire 474 has rails 476 that guide the expansion of the frame 205. The rails 476 extending around the sides of the frame 205 act as a spring that biases the frame 205 toward its closed position. The wire 474 defines the trajectory for translation of the sides of the frame.

Figure 41:
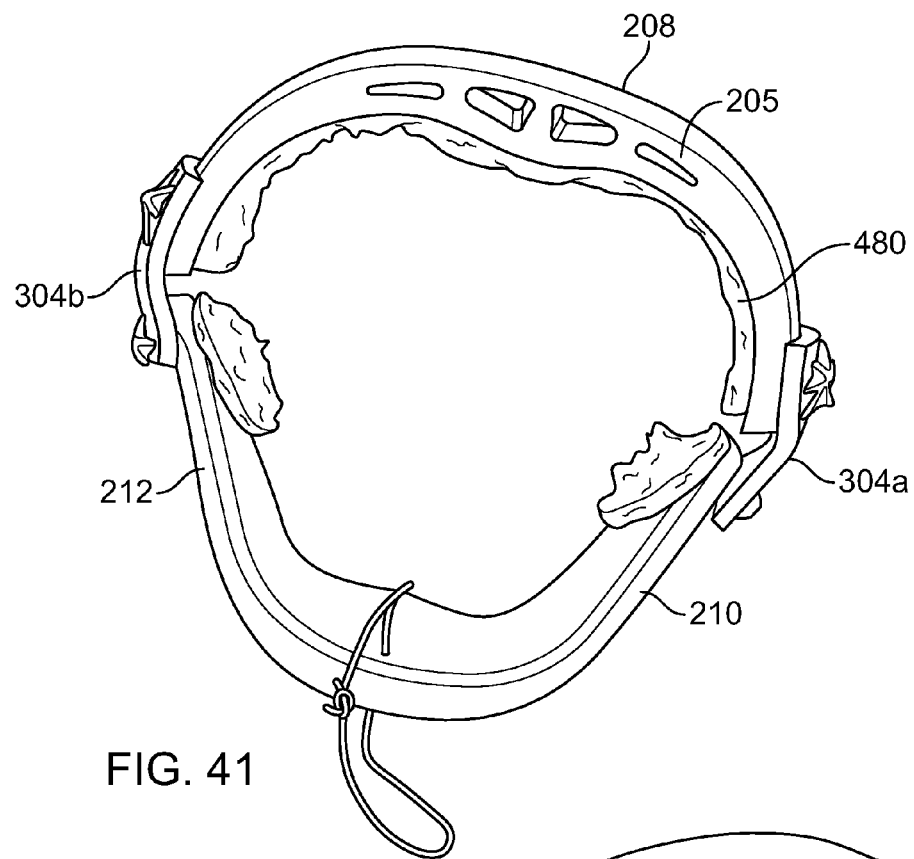
Figure 42:
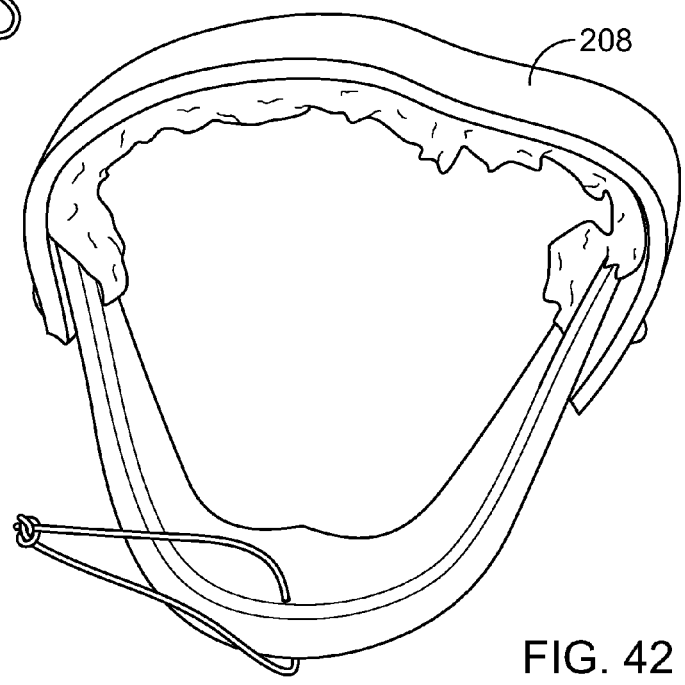

Referring to FIG. 41, rather than bristles, a buf-puf or scouring pad 480 made from a non-woven nylon fiber material stabilized with an epoxy can be used to engage the tongue. In the embodiment of FIG. 41, the frame 205 is split in the areas where rear region 208 meets side regions 210 and 212. Biasing members 304a, 304b span the gaps. Rather than having two gaps, the frame can be split in only one of the areas forming only one gap. In the embodiment of FIG. 42, the rear region 208 is formed by an elastic material with a buf-puf covering.

Figure 43A:
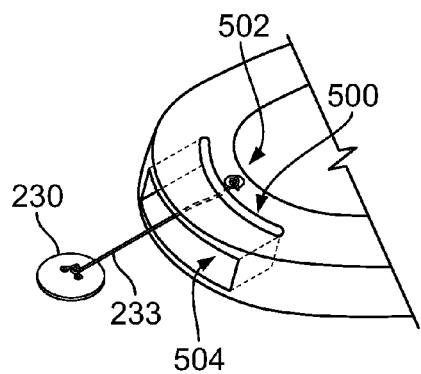
FIGS. 43A, 43B, 44 and 45 illustrate alternative embodiments of a tensioning mechanism.
Figure 43B:
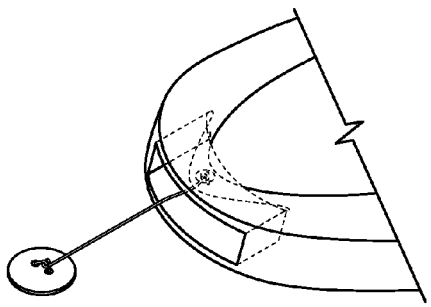
Figure 44:
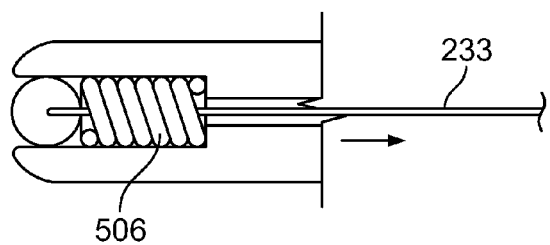
Figure 45:
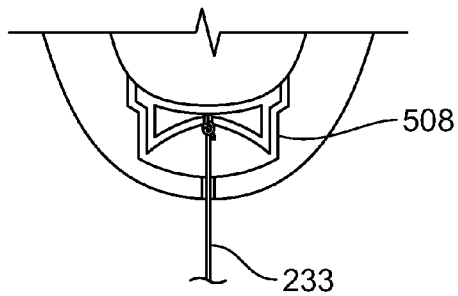

The bridge 238 can be positioned below the frame rather than above the frame. Rather than include a bridge 238, referring to FIGS. 43A and 43B, a relief cut 500 can be made in the frame to form a strut 502 to which the portion 233 is attached. The frame further defines a cavity 504 into which the strut 502 is pulled when tensioned. In the embodiment of FIG. 44, the portion 233 is attached to a spring 506 located within the frame. In the embodiment of FIG. 45, the portion 233 is attached to an internal flexure element 508 that can be a separately molded piece or metal element located within the frame. Alternatively, different fixed lengths of portion 233 between the anchor 230 and the tongue engagement element 204 can be provided to accommodate different users.

Figure 46:
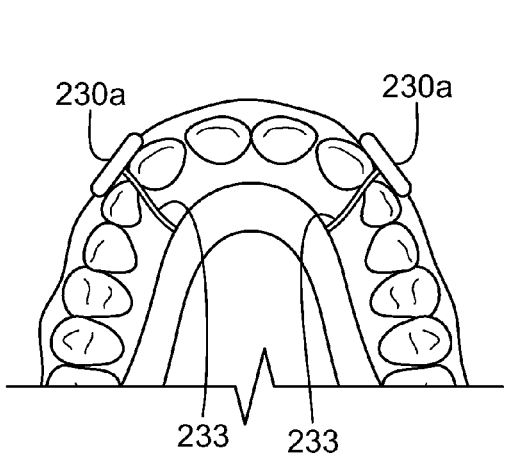
FIGS. 46 and 47 illustrate alternative embodiments of an anchor.
Figure 47:
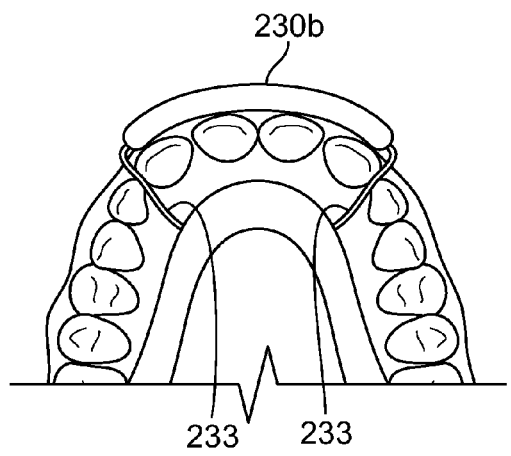

Rather than the single anchor 230, multiple primary anchors 230a (FIG. 46) or a broadly distributed anchor 230b (FIG. 47) can be employed to provide broader force distribution across the outer jaw and distribute the load across the tooth surface.

The oral appliance 200 can incorporate features for saliva removal by, for example, absorbing saliva within the mouth or transporting the saliva outside the mouth.

Figure 48:
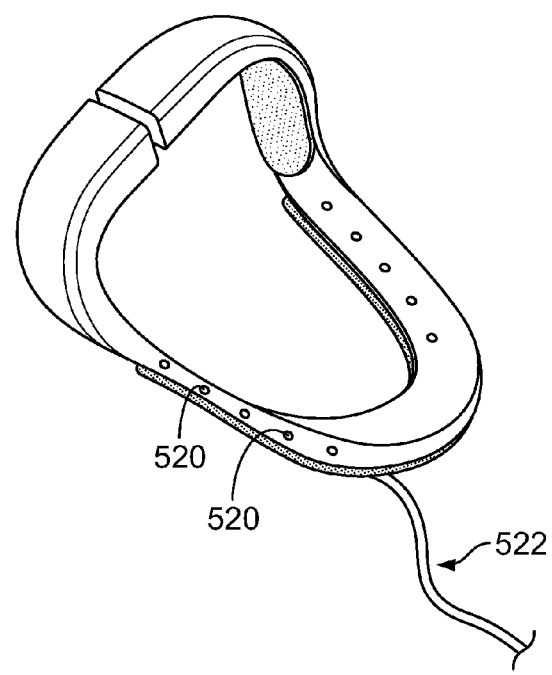
FIG. 48 illustrates an oral appliance incorporating a saliva removal device.

For the intra-oral option, the surface of the frame can be covered with a slow acting absorbent material. The saliva can be transported to a small reservoir that remains in the user's mouth. The extra-oral options could be active or passive devices. As illustrated in FIG. 48, for active devices, saliva is collected and sucked out of the mouth through suction holes 520 in the device by a tube 522 that is connected to a vacuum source. Passive devices may remove saliva via a tube as well. However, instead of connecting to a vacuum source, the passive device may remove saliva by wicking. The wicking tube has sufficient volume to capture saliva over one night. The wicking tube may be replaced daily or rinsed and prepped for subsequent use.

Figure 49:
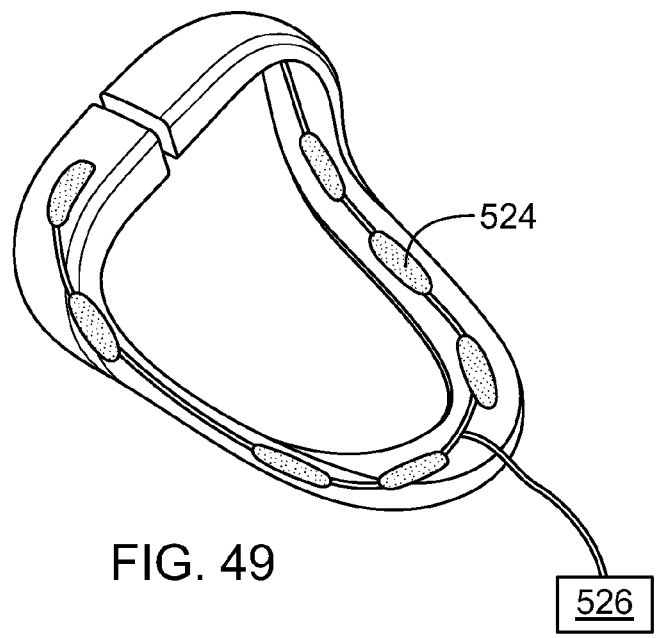
FIG. 49 illustrates an oral appliance incorporating a stimulation mechanism.

Several therapies exist to stimulate the hypoglossal nerve (HGN) during sleep, causing muscle contraction in the tongue and limiting airway collapse. These devices attach a lead to the HGN that feeds back to a pacemaker or similar generator device. Instead of implanting leads surgically to the HGN, leads 524 (FIG. 49) can be incorporated in the oral appliance to provide stimulation directly to the tongue. The leads can be connected to an external signal generator 526 or the signal generator can be on the oral appliance, worn intra-orally or implantable.

Figure 50:
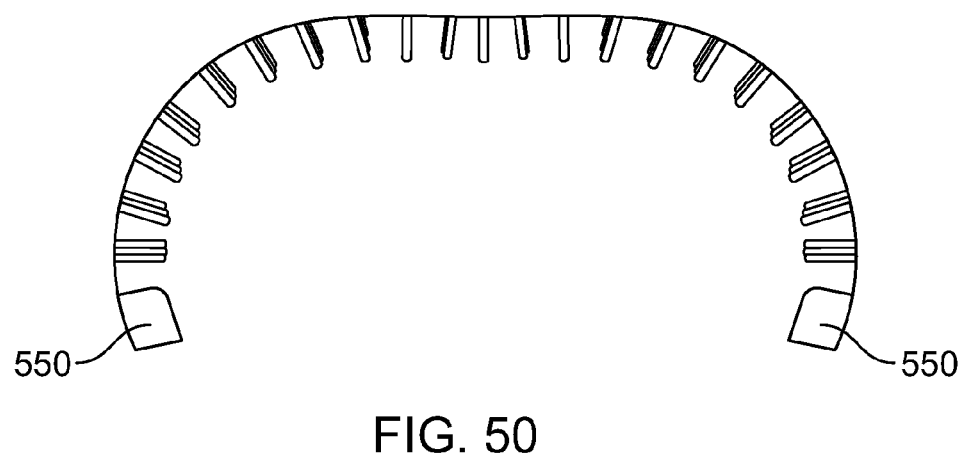
FIG. 50 illustrates another embodiment of a frame of an oral appliance.

Referring to FIG. 50, features 550 can be included on the inner surface of the frame 205 in the region where side regions 210, 212 meet piers 226, 228, respectively, and/or along side regions 210, 212. The features 550 act to push the tongue inward and upward into the bristles 220. The features 550 can have particular applicability for user's in which the tongue flattens when swallowing. The features 550 can be adjustable to customize the effect to a user's tongue, for example, by providing features 550 to the user of various sizes and shapes.

In order to assist with usage of an oral appliance, a bedside accessory acts as a unit to store and clean the oral appliance, to monitor the sleep, apnea or snoring of the user, to provide encouragement for compliance, and to connect the user with others via social networks. The unit can be battery operated and/or AC powered, include WiFi and/or cellular connectivity. The unit can include a UV light for cleaning/sterilizing the oral appliance when docked, detect snoring and/or apnea by microphone or laser vibrometry, measure compliance by tracking docking/undocking cycles, be equipped with RF or a Bluetooth sensor that is activated when worn (for example, the oral appliance detects that it is in fluid, or that the anchor is attached to the teeth) to further inform compliance, and upload data to a secure server for user evaluation and social media integration. The oral appliance can be equipped with RFID such that the bedside unit can detect when the oral appliance is being used and begin to collect data. If the user walks away from the unit such as to the bathroom sink to clean the device in the morning, the bedside unit will automatically stop recording sleep-related information.

Uploaded data can be used to educate the user. For example, if the information uploaded indicates that the oral appliance was not used, the user can be sent an email or a signal can be provided on the unit recommending that the oral appliance be used. If the information uploaded indicates abnormal breathing, the user can be sent an email or a signal can be provided on the unit recommending that the position of the oral appliance in use be checked to make sure the user is putting their tongue far enough forward in the oral appliance. The user can be provided a custom report from the uploaded data including, for example, an Apnea Hypopnea Index and an indication of their change in sleep performance. The user can be automatically sent a new appliance upon expiration. The oral appliance and unit can be used to measure sleep cycles and to activate an alarm to wake-up the user in a desired sleep cycle. The oral appliance can include a vibration mechanism to wake-up the user.

The features of different embodiments can be combined.

What is claimed is:

1. A method for securing a tongue engagement element in a user's mouth, comprising:
    moving an expanded tongue engagement element under a front region of a tongue and over a rear region of the tongue;
    allowing the tongue engagement element to return toward a non-expanded state, the tongue engagement element acting to resist rearward motion of the tongue; and
    configuring the tongue engagement element such that the tongue engagement element does not interfere with the user's normal bite.

2. The method of claim 1 wherein a tongue retention system of the tongue engagement element engages the tongue.

3. The method of claim 2 wherein the tongue retention system acts to resist rearward motion of the tongue.

4. The method of claim 1 further comprising placing a member connecting the tongue engagement element to an anchor between two teeth.

5. The method of claim 4 further comprising positioning the anchor between the user's teeth and the user's lip.

6. The method of claim 1 wherein a distal tip of the tongue is at rest while a pharyngeal portion of the tongue remains tensioned.

* * * * *